(12) United States Patent
Shiba et al.

(10) Patent No.: US 7,923,205 B2
(45) Date of Patent: Apr. 12, 2011

(54) METHOD FOR PROTECTING PERSONAL INFORMATION

(75) Inventors: Toshikazu Shiba, Tokyo (JP); Azuma Ohuchi, Hokkaido (JP)

(73) Assignee: Toshikazu Shiba, Tokyo (JP)

( * ) Notice: Subject to any disclaimer, the term of this patent is extended or adjusted under 35 U.S.C. 154(b) by 759 days.

(21) Appl. No.: 10/362,749

(22) PCT Filed: Aug. 24, 2001

(86) PCT No.: PCT/JP01/07267
§ 371 (c)(1),
(2), (4) Date: Jul. 22, 2003

(87) PCT Pub. No.: WO02/16605
PCT Pub. Date: Feb. 28, 2002

(65) Prior Publication Data
US 2004/0063111 A1  Apr. 1, 2004

(30) Foreign Application Priority Data

Aug. 25, 2000  (JP) ................................. 2000-256257

(51) Int. Cl.
*C12Q 1/68* (2006.01)
(52) U.S. Cl. .......................................................... 435/6
(58) Field of Classification Search .................. None
See application file for complete search history.

(56) References Cited

U.S. PATENT DOCUMENTS

| | | | | | |
|---|---|---|---|---|---|
| 4,839,142 | A | * | 6/1989 | Charm | 422/21 |
| 5,139,812 | A | * | 8/1992 | Lebacq | 427/7 |
| 5,234,811 | A | * | 8/1993 | Beutler et al. | 435/6 |
| 5,512,441 | A |   | 4/1996 | Ronai | |
| 5,571,905 | A | * | 11/1996 | Vogelstein et al. | 536/24.31 |
| 5,576,176 | A | * | 11/1996 | Adams et al. | 435/5 |
| 5,582,994 | A | * | 12/1996 | Carroll et al. | 435/6 |
| 5,677,152 | A | * | 10/1997 | Birch et al. | 435/91.2 |
| 5,830,655 | A | * | 11/1998 | Monforte et al. | 435/6 |
| 5,876,926 | A | * | 3/1999 | Beecham | 435/5 |
| 6,030,657 | A | * | 2/2000 | Butland et al. | 427/7 |
| 6,297,365 | B1 | * | 10/2001 | Adams et al. | 536/23.1 |
| 6,312,911 | B1 | * | 11/2001 | Bancroft et al. | 435/6 |
| 2002/0015937 | A1 | * | 2/2002 | Setcavage et al. | 435/2 |

FOREIGN PATENT DOCUMENTS

| DE | 19647811 A1 | * | 5/1998 |
|---|---|---|---|
| WO | WO 01/31551 A1 | | 3/2001 |

OTHER PUBLICATIONS

Kawazoe et al., "A Security System for Human Genome Information Encoded by Chemicals, Not by Electronic Codes," Genome Informatics, Dec. 2000, vol. 11, pp. 464-465.*
New England Biolabs 1998/99 Catalog (NEB Catalog).*
Darien T. Kadens, et al., "Pharmacogenomics: into the New Millennium", Drug Development Research, Apr. 2000, vol. 49, pp. 17-21.
Kahn, Scott M. et al.; "Rapid and sensitive nonradioactive detection of mutant K-*ras* genes vis 'enriched' PCR amplification"; *Oncogene*; 1991; pp. 1079-1083; vol. 6; Macmillan Press Ltd.
Martin, Paul and Jane Kaye; "The use of biological sample collections and personal medical information in human genetics research"; Background paper for the Wellcome Trust workshop on "*The Collection of Human Biological Samples for DNA and Other Analysis*"; Nov. 5, 1999; pp. 2-64; The Wellcome Trust; London.
Shigeo Mori, et al., "Kenkyu wo Mokuteki ni shita Byouri Kentai no Hozon-hou; Riyou-hou to so no Rinri-teki Soukumen", Gendai Iryou, Jan. 2001, vol. 33, No. 1, pp. 77-81.
Hitoshi Nomizu, et al., "Iden-sei Shuyou Screening ni okeru Idenshi Kensa no Genjo; Kazoku-sei Daichou Senshu-shou ni okeru Idenshi Kensa no Rinshou Ouyou", Rinshou Igaku, (1998), vol. 34, No. 3, pp. 331-337.

* cited by examiner

*Primary Examiner* — Christopher M. Babic
(74) *Attorney, Agent, or Firm* — Kilpatrick Townsend & Stockton LLP

(57) ABSTRACT

It is an objective of the present invention to provide a method capable of protecting personal information.
A method for protecting personal information that can be obtained by analyzing a biological sample is provided, wherein the method comprises adding to the biological sample a component obstructing the analysis of another component that provides personal information to be protected. Thus, the analysis of personal information such as genomic information without the person's consent can be technically prevented.
In addition, the present invention provides a technique for not only simply protecting personal information, but also for analyzing the once protected personal information as needed.

11 Claims, 13 Drawing Sheets

SEQUENCE LISTING

```
<160> NUMBER OF SEQ ID NOS: 33

<210> SEQ ID NO 1
<211> LENGTH: 128
<212> TYPE: DNA
<213> ORGANISM: Homo sapiens
```

```
<220> FEATURE:
<223> OTHER INFORMATION: portion of c-Ki-ras proto-oncogene of normal
      healthy subject (wild type(WT))

<400> SEQUENCE: 1
ttcctacagg aagcaagtag taattgatgg agaaacctgt ctcttggata ttctcgacac    60
agcaggtcaa gaggagtaca gtgcaatgag ggaccagtac atgaggactg gggagggctt   120
tctttgtg                                                            128

<210> SEQ ID NO 2
<211> LENGTH: 128
<212> TYPE: DNA
<213> ORGANISM: Artificial Sequence
<220> FEATURE:
<223> OTHER INFORMATION: Description of Artificial Sequence:dummy DNA,
      61st codon Lys

<400> SEQUENCE: 2
ttcctacagg aagcaagtag taattgatgg agaaacctgt ctcttggata ttctcgacac    60
agcaggtaaa gaggagtaca gtgcaatgag ggaccagtac atgaggactg gggagggctt   120
tctttgtg                                                            128

<210> SEQ ID NO 3
<211> LENGTH: 128
<212> TYPE: DNA
<213> ORGANISM: Artificial Sequence
<220> FEATURE:
<223> OTHER INFORMATION: Description of Artificial Sequence:dummy DNA,
      61st codon Glu

<400> SEQUENCE: 3
ttcctacagg aagcaagtag taattgatgg agaaacctgt ctcttggata ttctcgacac    60
agcaggtgaa gaggagtaca gtgcaatgag ggaccagtac atgaggactg gggagggctt   120
tctttgtg                                                            128

<210> SEQ ID NO 4
<211> LENGTH: 128
<212> TYPE: DNA
<213> ORGANISM: Artificial Sequence
<220> FEATURE:
<223> OTHER INFORMATION: Description of Artificial Sequence:dummy DNA,
      61st codon Arg

<400> SEQUENCE: 4
ttcctacagg aagcaagtag taattgatgg agaaacctgt ctcttggata ttctcgacac    60
agcaggtcga gaggagtaca gtgcaatgag ggaccagtac atgaggactg gggagggctt   120
tctttgtg                                                            128

<210> SEQ ID NO 5
<211> LENGTH: 128
<212> TYPE: DNA
<213> ORGANISM: Artificial Sequence
<220> FEATURE:
<223> OTHER INFORMATION: Description of Artificial Sequence:dummy DNA,
      61st codon Pro

<400> SEQUENCE: 5
ttcctacagg aagcaagtag taattgatgg agaaacctgt ctcttggata ttctcgacac    60
agcaggtcca gaggagtaca gtgcaatgag ggaccagtac atgaggactg gggagggctt   120
tctttgtg                                                            128
```

-continued

```
<210> SEQ ID NO 6
<211> LENGTH: 128
<212> TYPE: DNA
<213> ORGANISM: Artificial Sequence
<220> FEATURE:
<223> OTHER INFORMATION: Description of Artificial Sequence:dummy DNA,
      61st codon Leu

<400> SEQUENCE: 6
ttcctacagg aagcaagtag taattgatgg agaaacctgt ctcttggata ttctcgacac      60
agcaggtcta gaggagtaca gtgcaatgag ggaccagtac atgaggactg gggagggctt    120
tctttgtg                                                             128

<210> SEQ ID NO 7
<211> LENGTH: 128
<212> TYPE: DNA
<213> ORGANISM: Artificial Sequence
<220> FEATURE:
<223> OTHER INFORMATION: Description of Artificial Sequence:dummy DNA,
      61st codon His

<400> SEQUENCE: 7
ttcctacagg aagcaagtag taattgatgg agaaacctgt ctcttggata ttctcgacac      60
agcaggtcat gaggagtaca gtgcaatgag ggaccagtac atgaggactg gggagggctt    120
tctttgtg                                                             128

<210> SEQ ID NO 8
<211> LENGTH: 128
<212> TYPE: DNA
<213> ORGANISM: Artificial Sequence
<220> FEATURE:
<223> OTHER INFORMATION: Description of Artificial Sequence:dummy DNA,
      61st codon His

<400> SEQUENCE: 8
ttcctacagg aagcaagtag taattgatgg agaaacctgt ctcttggata ttctcgacac      60
agcaggtcac gaggagtaca gtgcaatgag ggaccagtac atgaggactg gggagggctt    120
tctttgtg                                                             128

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:key primer,
      Primer F

<400> SEQUENCE: 9
ttcctacagg aagcaagtag                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:key primer,
      Primer D

<400> SEQUENCE: 10
cacaaagaaa gccctcccca                                                  20

<210> SEQ ID NO 11
<211> LENGTH: 128
```

```
<212> TYPE: DNA
<213> ORGANISM: Artificial Sequence
<220> FEATURE:
<223> OTHER INFORMATION: Description of Artificial Sequence:dummy DNA
      having two single nucleotide substituted portions

<400> SEQUENCE: 11
ttcctacagg aagcaagtaa taattgatgg agaaacctgt ctcttggata ttctcgacac    60
agcaggtcga gaggagtaca gtgcaatgag ggaccagtac atgaggacag gggagggctt   120
tctttgtg                                                            128

<210> SEQ ID NO 12
<211> LENGTH: 128
<212> TYPE: DNA
<213> ORGANISM: Artificial Sequence
<220> FEATURE:
<223> OTHER INFORMATION: Description of Artificial Sequence:dummy DNA
      having two single nucleotide substituted portions

<400> SEQUENCE: 12
ttcctacagg aagcaagtac taattgatgg agaaacctgt ctcttggata ttctcgacac    60
agcaggtcga gaggagtaca gtgcaatgag ggaccagtac atgaggaccg gggagggctt   120
tctttgtg                                                            128

<210> SEQ ID NO 13
<211> LENGTH: 128
<212> TYPE: DNA
<213> ORGANISM: Artificial Sequence
<220> FEATURE:
<223> OTHER INFORMATION: Description of Artificial Sequence:dummy DNA
      having two single nucleotide substituted portions

<400> SEQUENCE: 13
ttcctacagg aagcaagtac taattgatgg agaaacctgt ctcttggata ttctcgacac    60
agcaggtcga gaggagtaca gtgcaatgag ggaccagtac atgaggacag gggagggctt   120
tctttgtg                                                            128

<210> SEQ ID NO 14
<211> LENGTH: 128
<212> TYPE: DNA
<213> ORGANISM: Artificial Sequence
<220> FEATURE:
<223> OTHER INFORMATION: Description of Artificial Sequence:dummy DNA
      having two single nucleotide substituted portions

<400> SEQUENCE: 14
ttcctacagg aagcaagtaa taattgatgg agaaacctgt ctcttggata ttctcgacac    60
agcaggtcta gaggagtaca gtgcaatgag ggaccagtac atgaggacag gggagggctt   120
tctttgtg                                                            128

<210> SEQ ID NO 15
<211> LENGTH: 128
<212> TYPE: DNA
<213> ORGANISM: Artificial Sequence
<220> FEATURE:
<223> OTHER INFORMATION: Description of Artificial Sequence:dummy DNA
      having two single nucleotide substituted portions

<400> SEQUENCE: 15
ttcctacagg aagcaagtac taattgatgg agaaacctgt ctcttggata ttctcgacac    60
agcaggtcta gaggagtaca gtgcaatgag ggaccagtac atgaggaccg gggagggctt   120
```

-continued tctttgtg    128

<210> SEQ ID NO 16
<211> LENGTH: 128
<212> TYPE: DNA
<213> ORGANISM: Artificial Sequence
<220> FEATURE:
<223> OTHER INFORMATION: Description of Artificial Sequence:dummy DNA
      having two single nucleotide substituted portions

<400> SEQUENCE: 16
ttcctacagg aagcaagtac taattgatgg agaaacctgt ctcttggata ttctcgacac    60
agcaggtcta gaggagtaca gtgcaatgag ggaccagtac atgaggacag gggagggctt    120
tctttgtg    128

<210> SEQ ID NO 17
<211> LENGTH: 128
<212> TYPE: DNA
<213> ORGANISM: Artificial Sequence
<220> FEATURE:
<223> OTHER INFORMATION: Description of Artificial Sequence:dummy DNA
      having two single nucleotide substituted portions

<400> SEQUENCE: 17
ttcctacagg aagcaagtaa taattgatgg agaaacctgt ctcttggata ttctcgacac    60
agcaggtcca gaggagtaca gtgcaatgag ggaccagtac atgaggacag gggagggctt    120
tctttgtg    128

<210> SEQ ID NO 18
<211> LENGTH: 128
<212> TYPE: DNA
<213> ORGANISM: Artificial Sequence
<220> FEATURE:
<223> OTHER INFORMATION: Description of Artificial Sequence:dummy DNA
      having two single nucleotide substituted portions

<400> SEQUENCE: 18
ttcctacagg aagcaagtac taattgatgg agaaacctgt ctcttggata ttctcgacac    60
agcaggtcca gaggagtaca gtgcaatgag ggaccagtac atgaggaccg gggagggctt    120
tctttgtg    128

<210> SEQ ID NO 19
<211> LENGTH: 128
<212> TYPE: DNA
<213> ORGANISM: Artificial Sequence
<220> FEATURE:
<223> OTHER INFORMATION: Description of Artificial Sequence:dummy DNA
      having two single nucleotide substituted portions

<400> SEQUENCE: 19
ttcctacagg aagcaagtac taattgatgg agaaacctgt ctcttggata ttctcgacac    60
agcaggtcca gaggagtaca gtgcaatgag ggaccagtac atgaggacag gggagggctt    120
tctttgtg    128

<210> SEQ ID NO 20
<211> LENGTH: 134
<212> TYPE: DNA
<213> ORGANISM: Artificial Sequence
<220> FEATURE:
<223> OTHER INFORMATION: Description of Artificial Sequence:analytical
      results of nucleotide sequence of PCR fragment
      amplified using primer F, DNA from blood
      containing no dummy DNA

```
<220> FEATURE:
<221> NAME/KEY: modified_base
<222> LOCATION: (1)..(134)
<223> OTHER INFORMATION: n = g, a, c or t

<400> SEQUENCE: 20
tantgnggag acctgtctct tggtattctc gacacagcag gtcaagagga gtacagtgca      60
atgagggacc agtacatgag gactggggag ggctttcttt gtgaacctgc aggcatgcaa     120
gcttggcgta atca                                                      134

<210> SEQ ID NO 21
<211> LENGTH: 134
<212> TYPE: DNA
<213> ORGANISM: Artificial Sequence
<220> FEATURE:
<223> OTHER INFORMATION: Description of Artificial Sequence:analytical
      results of nucleotide sequence of PCR fragment
      amplified using primer F, DNA from blood
      containing dummy DNA
<220> FEATURE:
<221> NAME/KEY: modified_base
<222> LOCATION: (1)..(134)
<223> OTHER INFORMATION: n = g, a, c or t

<400> SEQUENCE: 21
tantgnggag ancctgtctc ttggaattct cgacacagca ggtctagagg agtacagtgc      60
aatgagggac cagtacatga ggactgggga gggctttctt tgtgaacctg caggcatgca     120
agcttggcgt aatc                                                      134

<210> SEQ ID NO 22
<211> LENGTH: 133
<212> TYPE: DNA
<213> ORGANISM: Artificial Sequence
<220> FEATURE:
<223> OTHER INFORMATION: Description of Artificial Sequence:analytical
      results of nucleotide sequence of PCR fragment
      amplified using primer F, DNA from blood
      containing dummy DNA removed by streptavidin-bound
      magnetic beads
<220> FEATURE:
<221> NAME/KEY: modified_base
<222> LOCATION: (1)..(133)
<223> OTHER INFORMATION: n = g, a, c or t

<400> SEQUENCE: 22
tantgtggag anctgtctct tggaattctc gacacagcag gtcaagagga gtacagtgca      60
atgagggacc agtacatgag gactggggag ggctttcttt gtgaacctgc aggcatgcaa     120
gcttggcgta atc                                                       133

<210> SEQ ID NO 23
<211> LENGTH: 136
<212> TYPE: DNA
<213> ORGANISM: Artificial Sequence
<220> FEATURE:
<223> OTHER INFORMATION: Description of Artificial Sequence:analytical
      results of nucleotide sequence of PCR fragment
      amplified using primer F, DNA from blood
      containing dummy DNA
<220> FEATURE:
<221> NAME/KEY: modified_base
<222> LOCATION: (3)
<223> OTHER INFORMATION: n = g, a, c or t

<400> SEQUENCE: 23
tgnggagaac ctgtctcttg gtattctcga cacagcaggt caagaggagt acagtgcaat      60
gagggaccag tacatgagga ctggggaggg ctttctttgt gaacctgcag gcatgcaagc     120
```
ttggcgtaat catggt 136

<210> SEQ ID NO 24
<211> LENGTH: 135
<212> TYPE: DNA
<213> ORGANISM: Artificial Sequence
<220> FEATURE:
<223> OTHER INFORMATION: Description of Artificial Sequence:analytical
      results of nucleotide sequence of PCR fragment
      amplified using primer F, DNA from blood
      containing dummy DNA
<220> FEATURE:
<221> NAME/KEY: modified_base
<222> LOCATION: (3)
<223> OTHER INFORMATION: n = g, a, c or t

<400> SEQUENCE: 24
tgnggagaac tgtctcttgg tattctcgaa cagcaggtca agaggagtac agtgcaatga    60
gggaccagta catgaggact ggggagggct ttctttgtga acctgcaggc atgcaagctt   120
ggcgtaatca tggtc                                                    135

<210> SEQ ID NO 25
<211> LENGTH: 130
<212> TYPE: DNA
<213> ORGANISM: Artificial Sequence
<220> FEATURE:
<223> OTHER INFORMATION: Description of Artificial Sequence:analytical
      results of nucleotide sequence of PCR fragment
      amplified using primer F, DNA from blood
      containing dummy DNA
<220> FEATURE:
<221> NAME/KEY: modified_base
<222> LOCATION: (11)
<223> OTHER INFORMATION: n = g, a, c or t

<400> SEQUENCE: 25
tatgaggaga nctgctttgg aattctcgaa cagcaggtca agaggagtac agtgcaatga    60
gggaccagta catgaggact ggggagggct ttctttgtga acctgcaggc atgcaagctt   120
ggcgtaatca                                                          130

<210> SEQ ID NO 26
<211> LENGTH: 139
<212> TYPE: DNA
<213> ORGANISM: Artificial Sequence
<220> FEATURE:
<223> OTHER INFORMATION: Description of Artificial Sequence:analytical
      results of nucleotide sequence of PCR fragment
      amplified using primer D, DNA from blood
      containing dummy DNA
<220> FEATURE:
<221> NAME/KEY: modified_base
<222> LOCATION: (1)..(139)
<223> OTHER INFORMATION: n = g, a, c or t

<400> SEQUENCE: 26
gnctcatgtc tggtccctca ttgcactgta ctcctctnga cctgctgtgt ccgagaatat    60
ccaagagaca ggtttctcca tcaattacta cttgcttcct gtaggaagcc gctanngcca   120
tcancactcc ccngcttgc                                                139

<210> SEQ ID NO 27
<211> LENGTH: 134
<212> TYPE: DNA
<213> ORGANISM: Artificial Sequence
<220> FEATURE:
<223> OTHER INFORMATION: Description of Artificial Sequence:analytical
      results of nucleotide sequence of PCR fragment amplified using primer F, DNA from blood
containing dummy DNA removed by protein
G-Sepharose
<220> FEATURE:
<221> NAME/KEY: modified_base
<222> LOCATION: (3)
<223> OTHER INFORMATION: n = g, a, c or t

<400> SEQUENCE: 27
tgnggagacc tgtctcttgg aattctcgaa cagcaggtca agaggagtac agtgcaatga     60
gggaccagta catgaggact ggggagggct ttctttgtga acctgcaggc atgcaagctt    120
ggcgtaatca tggt                                                      134

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence:original DNA
      derived from biological sample without mismatched
      base bair

<400> SEQUENCE: 28
catcaattac tacttgcttc cagtaggaa                                       29

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence:dummy DNA-1
      with mismatched base pair

<400> SEQUENCE: 29
catcaattag tacttgcttc cagtaggaa                                       29

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence:dummy DNA-2
      with mismatched base pair

<400> SEQUENCE: 30
catcaattaa tacttgcttc cagtaggaa                                       29

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence:dummy DNA-3
      with mismatched base pair

<400> SEQUENCE: 31
catcaattat tacttgcttc cagtaggaa                                       29

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence:analytical
      result of nucleotide sequence of selective
      amplification of wild type DNA using key primer

<400> SEQUENCE: 32

```
gcaggtcaag ag                                                          12

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence:analytical
      result of nucleotide sequence of selective
      amplification of wild type DNA using key primer

<400> SEQUENCE: 33
ctcttgacct gc                                                          12
```

METHOD FOR PROTECTING PERSONAL INFORMATION

TECHNICAL FIELD

The present invention relates to a method for protecting personal information such as genetic information.

BACKGROUND ART

Each individual's genetic information recorded on genomic DNA is retained in the form of DNA. Such information is output via RNA as functional molecules such as proteins. Therefore, all genetic information may be regarded as having a chemical form, and at the same time, being an information medium. Although genetic information is not an electronic digital signal, a system for maintaining the security of that information is important when it comes to its safe maintenance.

Most organisms convert all the genetic information of each individual into a database and maintain that information within cells in chemical, molecular forms called genes. Genetic information is extracted from the database in the form of RNA anytime as needed, thus maintaining the activities supporting life. In multicellular organisms, every one of the cells constituting an individual, retains all the information of the whole individual in the form of genomic DNA. That is to say, an individual has as many copies of the database as the number of cells constituting the individual. Due to the presence of a great number of copies of information, maintaining the security poses an extremely difficult problem.

Among information retained in genomic DNA, there are many pieces of information requiring security. Currently, human genomic DNAs are being sequenced. The genetic information on genomic DNA naturally varies greatly between species, but there are also many slight differences even among individuals of the same species. Such differences are expressed as biological properties (phenotypes) of each individual. Phenotypes ranging from life span to a risk for contracting a specific disorder, and also as far as certain personalities, are said to be influenced by genomic DNA. Such genetic predispositions may have a great social significance in some cases, and hence, such information requires a high level of security. For example, personal information on a genetic predisposition of having a high risk of contracting a disease should not be easily accessible to a third party.

Gradual elucidation of the genome structure is expected to lead to an increase in genetic information analysis. As a result, genetic information requiring secure maintenance is likely to continue to rise. Therefore, a technique capable of preventing the analysis of genetic information recorded in genomic DNA is important.

There are many pieces of important information not only in genomic DNA information, but also in personal information that can be elucidated by analyzing biological samples. For example, it is generally prohibited by law to test whether an individual is infected by a specific virus without the consent of that individual. If such information is allowed to be readily made public, the individual is likely to undergo social discrimination regardless of his or her personality or will. Therefore, the provision of a technique capable of managing information derived from biological samples is useful.

Despite the essential necessity for a security system for actively preventing the leakage of such personal information encoded by DNA or RNA or in other chemical molecular forms, no effective means for that purpose is available yet. There are many techniques for maintaining the security of genetic information obtained by analyzing each individual's DNA or RNA that have already been converted into electronic digital signals. Such electronic information can be controlled by a centralized management using a computer. However, it is impossible to maintain the security of information recorded as chemical substances such as DNA by using management techniques for electronic information, because the information source is held in cells constituting individuals. A large number of gene copies exist in a single individual, and, moreover, blood cells, mucous cells and the like can be readily collected. Furthermore, since techniques for culturing these harvested cells and amplifying genes are available, it may be impossible to maintain the information security on a cell unit level.

As a result, at present, information security is barely maintained solely by the rule or morale that tests are not to be conducted without a person's consent. Therefore, it is an important objective to provide a technique capable of more securely maintaining the security of such information that can be obtained from a living organism. Nowadays, when the genomic draft has already been revealed and the post-sequencing era is coming around the corner, the protection of genetic information is likely to become an extremely important issue.

DISCLOSURE OF THE INVENTION

It is an objective of the present invention to provide a method capable of protecting personal information, more specifically, a technique enabling the maintenance of the security of personal information that can be obtained by analyzing biological samples such as cells.

The present inventors thought that it would be possible to improve the security of a large amount of information, including genetic information, if the analysis of personal information conducted without informed consent can be technically prevented. In other words, they thought that what was needed for the safe maintenance of information was not systems that depend on social security maintenance systems such as rules, morals, and such, but a way to technically prevent the analysis of information. The inventors actively pursued studies on techniques capable of effectively preventing the analysis of biological samples, accomplishing the present invention. That is, the present invention relates to a method for protecting personal information and applications thereof as described below:

[1] A method for protecting personal information obtained by analyzing a biological sample, wherein said method comprises adding to the biological sample, a component that obstructs the analysis of another component that provides personal information to be protected.

[2] The method according to [1], wherein said personal information to be protected is genetic information.

[3] The method according to [2], wherein said component that provides genetic information is a nucleic acid or a protein.

[4] The method according to [3], wherein said nucleic acid is genome or mRNA.

[5] The method according to [4], wherein said component obstructing analysis is a DNA comprising a region having a nucleotide sequence that provides personal information.

[6] The method according to [5], wherein said nucleotide sequence that provides personal information contains a mutation.

[7] The method according to [4], wherein said component obstructing analysis is at least one of the DNA analysis obstructers selected from the group consisting of:

(a) a random primer,
(b) an inhibitor of the DNA-polymerase reaction,
(c) an inhibitor of nucleic acid synthesis, and
(d) a nuclease.

[8] A method for analyzing personal information protected by the method according to [1], wherein said method comprises the step of removing the obstruction of the component that was added to obstruct the analysis.

[9] The method according to [8], wherein said obstructing component is DNA, and wherein the method comprises the step of removing the obstruction of the DNA by selective separation, decomposition, or modification thereof.

[10] The method according to [9], wherein the method comprises the step of selectively separating said DNA by the affinity binding to a tag added in advance to the DNA.

[11] The method according to [10], wherein said tag is an affinity binding substance and/or an artificially added nucleotide sequence.

[12] The method according to [9], wherein said obstructing component is DNA comprising a restriction enzyme recognition sequence that is not present in the nucleotide sequence to be analyzed, and wherein said method comprises the step of removing the obstruction by reacting with a restriction enzyme to selectively decompose the DNA.

[13] The method according to [8], wherein said method comprises the steps of:
(a) adding to a biological sample a DNA comprising (i) a nucleotide sequence that provides personal information and (ii) a mutation as the component that obstructs the analysis,
(b) analyzing the nucleotide sequence that provides personal information of a nucleic acid contained in said biological sample using a primer and/or probe, wherein said primer and/or probe is capable of hybridizing to the nucleic acid derived from the biological sample, but the hybridization to the DNA added in step (a) is inhibited due to the mutation contained in said DNA, and
(c) analyzing personal information contained in the nucleic acid derived from the biological sample using the hybridization level of said probe and/or primer as an index.

[14] A kit for analyzing protected personal information, which comprises a means for removing the obstructing action of the component added to obstruct the analysis.

[15] A biological sample-collecting vessel for protecting personal information obtained by analyzing a biological sample, wherein said vessel is filled in advance with a component that obstructs the analysis of another component that provides the personal information to be protected.

[16] The vessel according to [15] provided with a means for indicating that the analysis of the component that provides personal information to be protected has been obstructed.

[17] The vessel according to [15] further provided with a means for indicating information necessary for removing said obstruction.

[18] The vessel according to [17], wherein said indication has been encoded.

[19] A database that connects (a) biological sample-collecting vessels for protecting personal information that can be obtained by analyzing a biological sample, wherein the vessels are filled in advance with a component that obstructs the analysis of another component that provides personal information to be protected, and (b) a means necessary for removing the influence of said obstructing component for each of the vessels.

[20] A method for protecting personal information, wherein the method comprises the steps of:
(1) connecting (a) biological sample-collecting vessels for protecting personal information that can be obtained by analyzing a biological sample, wherein the vessels are filled in advance with a component that obstructs the analysis of another component that provides personal information to be protected, with (b) a means necessary for removing the influence of said obstructing component for each of the vessels, and
(2) disclosing, according to a request from an individual who requires analysis, a means necessary for removing the influence of said obstructing component for a specific vessel.

[21] A sample-analyzing device provided with the following means:
a) a means for reading an indication on a biological sample-collecting vessel that (a) is equipped with a means for indicating information capable of specifying the vessel, and (b) is a biological sample-collecting vessel for protecting personal information obtained by analyzing a biological sample, wherein said vessel is filled in advance with a component that obstructs the analysis of another component that provides personal information to be protected,
b) a means for disclosing a means necessary for removing the influence of an obstructing component contained in said vessel by inquiring the database according to [19] about information capable of specifying the vessel,
c) a means for implementing the means disclosed by the means of b) that is necessary for removing the obstruction, and
d) a means for analyzing the biological sample.

[22] The device according to [21], which comprises inquiring the database according to [19] about information capable of specifying a vessel via a network.

[23] A test sample-analyzing device equipped with the following means:
a) a means for reading an indication on a biological sample-collecting vessel equipped with a means for indicating information necessary for removing the influence of an obstructing means, wherein said vessel for protecting personal information that can be obtained by analyzing a biological sample has been filled in advance with a component that obstructs the analysis of another component that provides personal information to be protected,
b) a means for implementing a means necessary for removing the obstruction based on information read in step a), and
c) a means for analyzing the test sample.

[24] The analytical device according to [23], which comprises a means for decoding the encoded information necessary for removing the influence of said obstruction means.

[25] The analytical device according to [24] comprising a means for inquiring about information necessary for the decoding via a network.

[26] A method for analyzing a biological sample, wherein the method comprises:
a) reading an indication on a vessel for collecting a biological sample equipped with a means for indicating information capable of specifying said vessel for protecting personal information obtained by analyzing a biological sample, wherein said vessel has been filled in advance with a component that obstructs the analysis of another component that provides personal information to be protected,
b) disclosing a means necessary for removing the influence of a obstructing component contained in said vessel by inquiring the database according to [19] about information capable of specifying the vessel,
c) implementing the means necessary for removing the obstruction based on the information read in step b), and
d) analyzing the sample.

[27] A method for analyzing a biological sample, wherein the method comprises:

a) reading an indication on a biological sample-collecting vessel equipped with a means for indicating information necessary for removing the influence of an obstructing means, wherein said vessel for protecting the personal information obtained by analyzing said biological sample has been filled in advance with a component that obstructs the analysis of a component that provides the personal information to be protected,
b) implementing a means necessary for removing the obstruction based on the information read in step a), and
c) analyzing the sample.

A biological sample as referred to in the present invention means all kinds of samples that can be analyzed, which are obtained from living organisms and contain chemical substances that provide information on the organism. Normally, biological samples can be obtained by collecting tissues and body fluids constituting the body or excrements of an organism. Tissues may be derived from every organ, skin, mucous membrane, hair, tooth, nail, etc. Examples of body fluids are blood, sperm, mucus, digestive fluids such as saliva, bile, gastric juice, and the like. Furthermore, among excrements, sweat, feces, urine, and the like, are used as biological samples.

In the present invention, a chemical substance that provides information on a living organism refers to a chemical substance whose analysis provides some sort of information on the organism. Herein, a chemical substance means a substance having a molecular form. Therefore, a variety of organic compounds including nucleic acids and proteins are all chemical substances regardless of whether the structure and function have been elucidated or not. On the other hand, information that has been once analyzed and recorded in electronic media is not included in the chemical substances of the present invention.

A chemical substance that provides information on an organism is a substance whose analysis provides some sort of information on the organism. Analysis of a chemical substance as described in the present invention refers to acquiring information on the chemical substance derived from the above-described biological sample using any artificial method and converting the information to a manageable state. In other words, this analysis is an act that converts information held in the chemical substance into a form other than the original form. More specifically, analysis of a chemical substance can be defined as elucidating the physicochemical properties of the chemical substance itself, or the presence (absence) or the amount thereof.

Herein, the presence (absence) of a substance includes not only the presence (absence) of the substance at the time of analysis, but also the case of proving a trace of its presence (absence) in the past. In general, analysis of a substance means the analysis of the structure or presence of the substance, or the amount present, or such, but is not limited to these. More specifically, a biological sample generally comprises substances ranging from genomic DNA to RNA, proteins, various metabolites produced as a result of metabolisms by enzyme proteins, foreign compounds ingested by the individual and their metabolites, etc. All of these chemical substances can provide diverse pieces of information through the analysis of those substances. Personal information as used in the present invention is information that can be obtained by analyzing a biological sample, which is information on the living organism from which the biological sample derived from.

Hereinbelow, the process of decoding the genetic information will be described when the genetic information of a biological sample is DNA and RNA. First, normally, the amplification of only the necessary genetic information by PCR is required. PCR is performed using DNA extracted from a biological sample as a template or after converting an extracted RNA into DNA using reverse transcriptase. Using DNA fragments amplified by PCR, genetic information is analyzed. Examples of analytical methods are nucleotide sequence analysis of DNA and RNA, various electrophoretic methods (SSCP method, DNA finger printing method, RFLP method, etc.), methods based on hybridization to DNA, RNA, or PNA probes having a specific nucleotide sequence, methods using microarray such as DNA chips, methods using precise molecular weight measurement with mass spectrometry, methods based on techniques for analyzing bimolecular interactions, such as weight measurement using surface plasmon resonance, calorie meters, or quartz oscillators.

Alternatively, there are a number of analytical techniques based on principles different from that of the PCR method, such as the RCA (rolling circle amplification) method. The method for analyzing SNPs by the RCA method is well-known in the art. Furthermore, as a nucleic acid-analyzing technique based on a principle different from that of the PCR method, the NASBA method targeting RNA for analysis has been put to practical use. Furthermore, a method such as the SDA method for analyzing nucleic acids is also well-known in the art as a technique based on a principle different from that of PCR method. Although all of these analytical methods are different from the PCR method in the reaction principle, these methods and PCR are common in using nucleic acid synthetases such as DNA and RNA polymerases.

Furthermore, in the case of using a protein derived from a biological sample as a test sample for decoding genetic information, examples of analytical methods are: methods for analyzing the amino acid sequence of a target protein; methods for analyzing amino acid composition; immunological analytical methods using the antigen-antibody reaction; analytical methods using various chromatographies; analytical methods utilizing microarrays using protein chips; analytical methods based on precise molecular weight measurement by mass spectrometry; analytical methods using a technique for analyzing bimolecular interactions such as the weight measurement using surface plasmon resonance, calorie meters, quartz oscillators, etc.

Chemical substances, and information that can be obtained by the analysis thereof, will be more specifically described hereinbelow. Nucleic acids are important as chemical substances holding genetic information. The form of variations in the genetic information for each individual as described in the present invention includes: differences due to single nucleotide substitutions in genomic DNA [Single Nucleotide Polymorphisms (SNPs)]; differences due to the substitution of one nucleotide or more; frameshifts due to the insertion and deletion of nucleotides; differences in the repeating number of tandemly repeated sequences (variable number tandem repeat (VNTR)); deletions, duplications, and inversions of specific DNA regions; segmentation of genetic information due to the insertion of transposons, viruses, etc.; and the like. These variations induce differences in the properties of each individual. There are two types of such variations, one type being congenital while the other type appears as a variation in genetic information in certain cells in the form of a postnatal mutation. Postnatal mutagenesis is a major cause for serious disorders such as cancer. In addition, genetic information such as microsatellite markers that can be used as indexes for specific genetic characteristics is also important.

It is also possible to obtain, from a sample collected from a living body, not only genetic information on the living organism itself, but also information on other living organisms that are infecting (or parasitic on) this living body. For example, the detection of a virus genome in a body fluid of a living body provides evidence of a virus infection. Furthermore, if the genetic information of a pathogenic bacterium is detected in the feces and urine, it will be evidence of a bacterial infection. When these facts of infection are required to be managed as information, the genetic information providing the evidence becomes personal information that should be protected by the present invention.

In the present invention, the protection of personal information is achieved by adding to the biological sample a component that obstructs the analysis of a chemical substance that provides personal information to be protected. In other words, aiming at protecting information, this invention is established by intentionally obstructing the analysis of a chemical substance that provides information. The analysis of various chemical substances has shown the presence of components that obstruct the analysis. However, no technique that intentionally obstructs the analysis aiming at the protection of personal information was known. In the present invention, the achievement of the protection of a particular information by obstructing the analysis of a chemical substance is called "locking."

Furthermore, in this invention, the recovery of a once obstructed analysis to an analyzable state by any means is termed "unlocking." Locking can be achieved, for example, by techniques such as interfering with analytical results, obstructing the reaction of analysis, removing or decomposing a chemical substance to be analyzed, and so on. Protection of personal information can be achieved by locking. Therefore, a method for protecting personal information in the present invention aims at achieving the locking of information, regardless of whether the unlocking is possible or not.

However, in a specific embodiment of the present invention, the unlocking of information is also possible. That is, this invention provides a method for analyzing personal information that has been protected by the above-described means, in which the method comprises the step of removing the obstruction of the aforementioned component that has been added for obstructing the analysis. For example, when the locking is achieved by interfering with analytical results or obstructing the reaction of analysis, the unlocking can be realized by removing the cause of the locking. More specifically, the locking and the unlocking can be achieved, for example, by the following techniques. When the decoding of personal information is irreversibly locked, this locking is not required to be unlocked. However, by making the unlocking possible, it is possible, for example, to allow only a specific authorized organization to decode the personal information. Furthermore, this unlocking enables flexible operation of the information management system in that it allows the analysis of information with a personal authorization as a prerequisite. Alternatively, the unlocking system makes it possible to respond in emergency situations when the analysis of information must take precedence over an individual's wish.

A method for protecting personal information by obstructing the analysis of a gene represented by genomic DNA using the gene as a chemical substance will be specifically described hereinbelow. Genetic variations for each individual are recorded (encoded) on genomic DNA in the form of nucleotide sequences. Furthermore, a portion of information-read from the genomic DNA is encoded in RNA. Analysis is performed by artificially decoding the information encoded in these DNA and RNA. Nowadays, the analyses of DNA or RNA are mostly carried out by using their annealing to probes and/or primers, the enzymatic reaction with DNA or RNA polymerases, etc. Therefore, if it were possible to obstruct these reactions themselves or interfere with analytical results, it would be possible to obstruct the analysis of the DNA or RNA. In the present invention, a component capable of obstructing DNA analysis is termed a DNA analysis obstructer.

Locking Genetic Information with Dummy DNA

It is possible to lock information by artificially adding a nucleic acid such as DNA or RNA to a biological sample. In the present invention, such artificially added nucleic acids are generically called dummy DNAs.

A dummy DNA to be added may comprise a wild-type nucleotide sequence or a plurality of genetic variations. Furthermore, a dummy DNA having a nucleotide sequence that should not normally exist may be also added. In general, the more variations a dummy DNA has, the more securely the obstruction of gene analysis can be achieved. It is desirable to add a dummy DNA in an amount that exceeds the amount of DNA present in the individual from which the biological sample is derived. For example, when nucleic acid molecules comprising a plurality of nucleotide sequence types are artificially added as dummy DNA, they are excessively added so that the total amount of the added dummy DNA exceeds that of the presumed total nucleic acid molecule amount contained in the biological sample. An excessive amount refers to at least an amount that is equal to, or more than, preferably two folds or more of, the amount of the gene in the test sample, where the gene is the object of analysis. In the case of using a dummy DNA to obstruct PCR, which may be referred to as the essential reaction for gene analysis at present, it is particularly effective to add an excessive dummy DNA amount of three-folds or more.

When DNA is extracted from a biological sample, purified and subjected to decoding, dummy DNAs completely conceals the DNA of the individual from whom the biological sample derived. When amplifying DNA by PCR in particular, dummy DNAs are dominantly amplified and locks the original information. Even if the decoding of genetic information is done without the help of the PCR amplification process, the presence of a dummy DNA in an excess amount will establish the locking of information. That is, the dummy DNA interferes with the DNA information of an individual from whom the biological sample derived, making the decoding of genetic information impossible, resulting in the locking of genetic information by the dummy DNA.

In one case, a dummy DNA may contain all the genetic information, whereas in another, it may contain, depending on the purpose, only a single or several specific pieces of genetic information. When containing all of the information, every information derived from the biological sample will be locked, while, in the case of containing merely a portion of genetic information, only the portion of information will be locked. That is, it is possible to selectively lock the genetic information to be locked according to the purpose.

It is desirable that a dummy DNA is structurally similar to the nucleic acid that is the object of analysis. Alternatively, the dummy DNA may be of the same species. For example, genomic DNA may be used for obstructing genome analysis, and RNA for obstructing RNA analysis. More specifically, to obstruct human genomic DNA analysis, the human genome can be used as a dummy DNA. As to human genomic DNA, when aiming at obstructing the analysis in a specific chromosome, a specific chromosome or fragments thereof may be added, or one or more sets of chromosomes may be used as dummies. In addition, when aiming at obstructing RNA analysis, it is also effective to use dummy RNA, or cDNA that will be definitely synthesized in the process of RNA analysis. In this case, as a dummy RNA, RNA obtained by in vitro synthesis using DNA as a template, or a natural RNA extracted from living cells, can be used.

Locking Genetic Information by a Random Primer

In contrast to confusing templates in a locking method by the addition of dummy DNA, a random primer may be added aiming at confusing primers. In contrast to a dummy DNA that achieves the locking of a particular gene analysis, locking by a random primer can be said to be a technique for locking the extraction of a particular genetic information by inhibiting gene amplification from a specific primer in PCR.

In the present invention, when nucleic acids such as dummy DNAs and random primers are used to obstruct gene information analysis, these nucleic acids can be added to biological samples in the form of a solution or a solid. In this case, locking of genetic information can be easily achieved by using a sample-collecting tool or vessel into which a dummy DNA has been filled in advance. To protect nucleic acids such as dummy DNAs, and the like, from the degradation action of nucleases and such, the dummy DNA may be enclosed in a protecting material.

More specifically, a dummy DNA can be protected by enclosing it in microcapsules, liposomes, macromolecules such as gels, etc. As a protecting material used in this invention, by selecting a material having a property that will be lost when cells are disrupted to extract DNA or RNA in order to release the enclosed dummy DNA, the obstructing action of the dummy DNA can be expressed at the instance of genetic information analysis. Examples of protecting materials satisfying such conditions are liposomes, microcapsules, etc.

Liposomes can be prepared, for example, by mixing phosphatidylcholine, phosphatidylglycerol, cholesterol, and such at appropriate weight ratios, followed by dispersing the resulting mixture in an aqueous solution of dummy DNA, etc. Furthermore, microcapsules made of agarose beads, mixtures of alginic acid and calcium, and the like, are well known. Methods for enclosing DNA or RNA in these protecting materials are also well known in the art. In the present invention, not only protecting materials, but also drugs, nuclease inhibitors, and such can be combined for stabilizing dummy DNA.

Locking Method Using a DNA Polymerase Inhibitor

As described above, at present, DNA and RNA polymerases can be said to be principle enzymes in gene analysis. They are important enzymes constituting a number of gene analytical techniques such as the PCR method, RCA method, NASBA method, SDA method, and the like. Therefore, mixing inhibitors of these enzymes in advance with a biological sample can interfere with gene analysis. As an enzyme inhibitor, an antibody against the enzyme, a chelating reagent, a protease that digests the enzyme protein, and the like, can be used.

The Method for Irreversibly Decomposing a Component that is the Objective of Analysis, or Converting the Component into a State that is Impossible to Analyze In the case where the unlocking of information is not intended, information can be locked by irreversibly decomposing the chemical substance that is the objective of analysis, or converting the substance into a state that cannot be analyzed. For example, genetic information can be made unanalyzable by decomposing the DNA with a digestive enzyme such as a nuclease. Since RNA in particular is easily decomposed by RNase, the enzymatic degradation thereof is effective as a technique for locking information.

Furthermore, compounds irreversibly inhibiting the synthesis of a nucleic acid by decomposing it, binding to it, or chemically modifying it, for example by alkylation, are also effective in locking information. As a compound of this type, a nucleic acid-targeting antibiotic can be used. More specifically, such compounds are exemplified by mitomycin, actinomycin, bleomycin, cisplatin, their derivatives, and the like. Furthermore, compounds such as nitrogen mustard and N-methyl-N'-nitrosoguanidine and the like can be used as compounds that inhibit the synthesis of nucleic acids by acylation thereof.

All the compounds cited so far are those that can lock information when they are mixed with biological samples. In contrast, a compound capable of locking information only under a specific condition can be also used in the present invention. For example, compounds such as the triphenanthroline-ruthenium complex, triphenanthroline-cobalt complex are known to show DNA cleavage activity when exposed to light. Furthermore, psoralen and derivatives thereof can be given as substances that inhibit the synthesis of DNA by binding thereto as a result of being exposed to light. The use of such compounds that are activated by exposure to light makes it possible to control the locking of information by light exposure. Therefore, for example, information can be locked by shading the system containing compounds such as those described above until the test is over and then exposing it to light.

Alternatively, it is also possible to lock information using compounds that react with DNA under heat. For example, after treating DNA in a biological sample with dimethyl sulfate, formic acid, sodium hydroxide, potassium permanganate, or such, piperidine is added, and the resulting mixture is heated at 90° C. for 30 min, or at a temperature lower than 90° C. for a long time, to cleave DNA and RNA, thereby inhibiting the synthesis.

In addition, a technique for inhibiting nucleic acid synthesis by a physical action can be used to lock information. For example, ultrasonic sound and irradiation of ultraviolet rays or radiation enables one to cleave nucleic acids so as to inhibit synthesis thereof.

These analysis-obstructing components or means can be used alone or in combination. By combining a plurality of obstructive actions to provide various obstructions, illegal analyses can be more surely prevented.

As already described, in a specific embodiment of the present invention, it is possible to unlock a biological sample that is in a locked state that resulted due to an obstruction of analysis. An embodiment in which the unlocking can be conducted will be specifically described hereafter. The unlocking can be achieved by removing or decomposing a substance that has been added to obstruct analysis, or by attenuating the obstructive action of the substance.

For example, when obstructing analysis with a dummy DNA, this dummy DNA can be removed or the obstructive action thereof can be attenuated by various methods. An example of a technique that enables the unlocking is, modifying the dummy DNA with a compound and removing the dummy DNA from the biological sample using this modifying compound (modifier). When obstructing analysis with a dummy DNA that functions as a template, the dummy DNA can be modified using any substance at any position, as long as the resulting modified dummy DNA can act as a template. Furthermore, in the case where dummy DNA acts as a primer, it can be modified with any substance at any position except for the 3'-end of the molecule.

By contacting the modified dummy DNA with a substance having affinity to the modifier, dummy DNA can be selectively absorbed and removed. Such a modifier is exemplified by a substance having a binding activity towards the affinity compound. More specifically, compounds such as biotin, digoxigenin, lectin, and the like, are known to have a binding activity towards their respective affinity substances. Dummy DNAs labeled with these compounds can be removed from a biological sample as described below.

That is, first, this affinity substance is added to DNA or RNA that has been extracted and purified from a biological sample. The use of an affinity substance that has been immobilized in advance on a carrier such as beads, or something that can be immobilized, makes the separation of dummy DNA easy. Dummy DNA binds to the affinity substance and precipitates in the solution. The precipitate is separated from the supernatant by centrifugation, or such, and removed. Dummy DNA can be almost completely removed by conducting this separation once to several times.

Furthermore, when the affinity substance is an antibody, it may be used as it is. In this case, using beads and the like on which a substance (e.g., protein A, protein G, etc.) having an affinity to the antibody is immobilized, the substance and the whole antibody bound thereto can be trapped and precipitated. By the above-described operation, the dummy DNA is removed from the DNA or RNA derived from the biological sample enabling the following PCR and decoding of its genetic information.

Even when a dummy DNA is modified with a plurality of compounds, it is possible to unlock information by repeating the above-described operation using affinity substances corresponding to each of the compounds. In the present invention, the unlocking can be achieved even when the dummy DNA is not completely removed. As shown in Examples, locking of genetic information by dummy DNA can be achieved more surely when the dummy DNA is present in as much amount as possible relative to the living organism-derived genetic material contained in the sample. In other words, the unlocking can be achieved if it is possible to create a situation in which dummy DNA is present only in a small amount relative to the amount of genetic information derived from the living organism. However, since genetic material deriving from a biological sample may not always be present in a sufficiently large amount, it is needless to say that the removal of dummy DNA as completely as possible is an essential condition for surely unlocking information.

When the removal of dummy DNA is made possible by absorption of a modifier, needless to say, information as to what the modifier is, must be strictly controlled. Leakage of this type of information may result in the undesirable unlocking of information by a third party. Furthermore, it is possible to make the illegal unlocking by a third party more difficult by mixing with several types of dummy DNAs modified by different compounds.

A dummy DNA can be removed not only through the binding of a modifier compound to an affinity substance, but also by hybridization. Hereinbelow, a method of incorporating into dummy DNA a specific nucleotide sequence for hybridization is described. DNAs bind to polynucleotides having complementary nucleotide sequences by hydrogen bonds. This binding can be made specific to a nucleotide sequence by performing hybridization under highly stringent conditions. Therefore, the addition to a dummy DNA a nucleotide sequence that is not present in a nucleic acid containing the genetic information to be analyzed, makes it possible to specifically remove the dummy DNA by hybridization. In this case, the probe used for removing the dummy DNA is bound in advance to a solid phase, or to a tag that can be trapped by a solid phase, and thereby, the dummy DNA is easily removed.

It is possible to unlock dummy DNA by a technique other than the modification thereof. Hereinbelow, a method for positioning a specific restriction enzyme recognition site in a dummy DNA will be described as an unlocking technique that does not rely on modification. For example, when information on gene A is the object of analysis, DNA having a nucleotide sequence similar to that of gene A is used as a dummy DNA. An arrangement of a restriction enzyme recognition site in the dummy DNA makes it possible to specifically cleave the dummy DNA by a restriction enzyme. The restriction enzyme used in this case is one that recognizes long nucleotide sequences which comprise, for example, six or more nucleotides, and which are clearly not present in gene A, the object of analysis. For example, when a biological sample that has already been locked is treated with a restriction enzyme prior to PCR, the dummy DNA is not amplified, but only the genetic substance derived from the living organism is. In the method using restriction enzymes, it is not necessary to chemically modify dummy DNA, which makes it easy to prepare the dummy DNA. Furthermore, when it is so arranged that the unlocking cannot be conducted unless a plurality of restriction enzymes are used, the certainty of information locking can be enhanced.

In this case, fragments of dummy DNA digested with a restriction enzyme have the restriction enzyme recognition sequence at the 3'-end. This results in dummy DNA fragments having nucleotide sequences different from those of the genetic substances derived from the living organism. When a primer is not completely complementary to a template at the 3'-end, it is understood that usually, such ends do not become replication origins for polymerases. Therefore, the possibility of the digested dummy DNA fragment acting as a primer and thus failing to achieve the unlocking is low.

To achieve the unlocking, it is also possible to use a probe and/or primer whose hybridization to dummy DNA is inhibited. That is, the present invention relates to a method of analyzing protected personal information, wherein the method comprises:

(a) adding to a biological sample a DNA comprising (i) a nucleotide sequence that provides personal information and (ii) a mutation as the component that obstructs the analysis,
(b) analyzing the nucleotide sequence that provides personal information of a nucleic acid contained in said biological sample using a primer and/or probe, wherein said primer and/or probe is capable of hybridizing to the nucleic acid derived from the biological sample, but the hybridization to the DNA added in step (a) is inhibited due to the mutation contained in said DNA, and
(c) analyzing personal information contained in the nucleic acid derived from the biological sample using the hybridization level of said probe and/or primer as an index.

In this method, as a dummy DNA, a DNA that comprises a nucleotide sequence corresponding to the sequence providing personal information, but also has a mutation therein is used. There is no limitation in the site and the number of mutations in the dummy DNA. A DNA having mutations in at least 1, usually 2 to 4, preferably 5 to 20 or 20 to 50 sites can be used as the dummy DNA. Sites of mutation may be consecutive or far apart. A dummy DNA having a plurality of mutations in a region likely to provide personal information to be protected, may be a suitable DNA in the present invention.

A region likely to provide personal information to be protected may be exemplified first by a region that will become the object for analyzing a polymorphism or mutation. Furthermore, in the present invention, a region to which a primer used for amplifying these objects anneals, is also included in the region likely to provide personal information to be protected. Primers are designed using a nucleotide sequence that flanks the objective region and is expected to specifically amplify such a region. Therefore, in general, a primer used for amplifying a particular region is often selected from a certain range on a target nucleotide sequence. Therefore, once the region likely to provide personal information is identified, it is possible to predict a region to which a primer necessary for analyzing that region anneals. Alternatively, DNA chips are expected to be used for the analysis. In this case, a DNA having a mutation in a region that will become the target of the DNA that is likely to be used as a probe in a DNA chip, is preferable as a dummy DNA.

A dummy DNA, when analyzed by a usual analytical technique, interferes with the analytical results of nucleic acids derived from the living organism so as to protect personal information. To carry out the analysis of personal information derived from the biological sample without being influenced by dummy DNA, key primers or key probes are used in the present invention. A key primer refers to a primer that is capable of functioning as a primer for DNA derived from the living organism, but is incapable of doing so for dummy DNA due to the mutation in the dummy DNA. Such a primer can be obtained, for example, by synthesizing an oligonucleotide comprising a nucleotide sequence so designed that the 3'-end of the primer is arranged to correspond to the mutation of the dummy DNA. The use of a key primer enables the specific synthesis of nucleic acids derived from the biological sample. Since it is impossible to design the nucleotide sequence of a key primer without knowing the exact site of mutation in the DNA added as the dummy DNA, the unlocking using the key primer is achieved.

Hereinbelow, a method for amplifying only a target DNA derived from a biological sample by PCR using a key primer will be described in detail. In this case, a mutation by a single nucleotide substitution of a predetermined nucleotide in the dummy DNA sequence is inserted in advance so that the dummy DNA differs from DNA derived from the biological sample. Thus, all dummy DNAs are different from DNA derived from the living organism at this mutation site in the nucleotide sequence. As shown in the example of FIG. 10, dummy DNAs have guanine (G) (FIG. 10, dummy DNA-1 (SEQ ID NO:29)), adenine (A) (FIG. 10, dummy DNA-2 (SEQ ID NO:30)), or thymine (T) (FIG. 10, dummy DNA-3 (SEQ ID NO:31)) at the site that generally has cytosine (C) in the DNA derived from the living organism (SEQ ID NO:28). When using a PCR primer whose 3'-end is capable of annealing to the aforementioned nucleotide portion, a mismatched base pair is formed between this primer and the dummy DNA at the 3'-end, making the amplification by PCR difficult. However, this primer completely anneals to the DNA derived from the living organism without forming mismatched base pairs, and thus, only the DNA derived from the living organism can be amplified. Such a primer is referred to as a key primer (SEQ ID NO:9), and it is impossible to selectively amplify DNA derived from a living organism without knowing the sequences of the two key primers that anneal to the upstream and downstream of the DNA region to be amplified.

If a number of point mutations are inserted into dummy DNAs to make them different from the DNA derived from a living organism, it is not easy to detect which mutations are common to all dummy DNAs. Therefore, for example, in the case of amplifying a target DNA of 1,000 bp, 200,000 or more different combinations of primers have to be tested to find the two key primers, making the search for them difficult.

Furthermore, key probes refer to, similar to key primes, DNAs comprising a nucleotide sequence which is capable of hybridizing to a DNA derived from a living organism, but the hybridization to dummy DNA is inhibited because of the mutation in the dummy DNA. Analysis using a DNA chip is conducted based on signal intensity compared to that of a mismatched probe (probe having a single base difference). That is, analysis is performed under conditions where the difference in one nucleotide can be distinguished as a difference in signal intensity. Therefore, using a key probe according to the present invention, it is possible to distinguish the signal of a dummy DNA having a single nucleotide difference from the signal of DNA derived from a living organism. This way, only a DNA chip containing the key probe can correctly analyze the locked biological sample. Thus, it is possible to unlock the information by the key probe.

It is also possible to obtain genetic information of a living organism not only from nucleic acids, but also from translation products thereof, namely, proteins. In some cases, mutations in the nucleotide sequence of a gene can be found by analyzing the amino acid sequence of the protein. Furthermore, it is also possible to find whether or not a protein has a particular mutation by analyzing the immunological reaction between the protein and an antibody, or a biological activity of the protein. Thus, chemical substances in the present invention that provide personal information to be protected include proteins.

When a protein derived from a biological sample is used to decode genetic information, it is possible to use a dummy protein to lock information, as in the case of nucleic acids. Since dummy proteins include wild type proteins and various mutant proteins, they are indistinguishable from proteins derived from the biological sample. Thus, it is impossible to extract only the information deriving from the biological sample.

Furthermore, it is possible to unlock information by removing a dummy protein using a method similar to that for dummy DNA. That is, the unlocking can be achieved by chemically modifying a dummy protein in advance using a modifier, and adding a substance having a specific affinity to that modifier to remove the dummy protein. As a dummy protein, a fusion protein to which a specific protein has been added may also be used. Fusion proteins can be easily obtained by a genetic engineering technique. When a protein added to form a fusion protein is an antigenic substance, it is possible to remove the dummy protein using an antibody recognizing this antigenic substance. Alternatively, if the modifier is a metallic ion affinity protein such as a histidine tag, it can be absorbed with a nickel column, or such. Alternatively, it is also possible to position beforehand, a specific protease-recognizing amino acid sequence in the amino acid sequence of a dummy protein to enzymatically decompose the protein.

In the present invention, to lock information that can be obtained from a protein, the analysis can be obstructed by modifying or denaturing the protein. Techniques for modifying and denaturing proteins are well known in the art. For example, proteins can be denatured by heat-treating a biological sample-containing protein. Furthermore, by reacting a protease with a biological sample, the protein is randomly digested so that the amino acid sequence becomes impossible to be analyzed.

The above-described technique using dummy molecules that can be applied to lock and unlock information derived from DNAs, RNAs, or proteins of living organisms, is applicable to all molecules contained in living organisms. Thus, it is also possible to control the acquisition of information of living organisms by measuring metabolites, hormones, enzyme activities, etc.

Reagent components necessary for a method based on this invention for analyzing protected personal information can be supplied as a kit assembled in advance. That is, the present invention provides a kit for analyzing protected personal information, which comprises a means for removing the obstruction of a component added to obstruct the analysis. The above-described means may be a single means, or a combination of several means. When the treatment for removing the obstruction can be conducted in a homogeneous system, a plurality of means may be combined to form a kit of the present invention. In the kit of the present invention, reagents necessary for analysis can be combined as needed.

For example, when a dummy DNA modified with an affinity substance is added, a kit comprising the binding partner for the affinity substance can be used. This kit may include a primer necessary for conducting the objective analysis. As described above, information can be effectively locked by using a combination of several compounds as affinity substances. To unlock information thus locked, a reagent comprising a combination of several binding partners is required.

To deal with such a situation, preparing a kit comprising in advance all required combinations of binding partners for unlocking reagents that can respond to various combinations of affinity substances, is important. A kit according to the present invention comprising a combination of binding partners may be given any name according to the combinations. The name of the kit is so arranged that the binding partner(s) constituting the kit cannot be predicted from the name. In this case, unlocking can be permitted by simply specifying the name of the kit necessary for the unlocking, without specifying the type of affinity substance modifying the dummy DNA used for locking. A third party cannot specify the binding partner necessary for the unlocking solely from the name of a kit. As a result, the security of personal information can be enhanced by controlling the distribution of the kit and information contained therein.

That is, the present invention relates to a kit that comprises several means for removing the obstruction of a component added to obstruct the analysis, and in which is set up several means constituting different combinations of the several means for removing the obstruction.

Alternatively, when DNA with a mutation is added as a dummy DNA, a kit comprising a key probe and/or key primer is used. In this case, the key primer and/or key probe, function as a means for removing the aforementioned obstruction, and at the same time, acts as a reagent necessary for conducting the objective analysis.

In the present invention, depending on the nucleotide sequence of the dummy DNA added to protect personal information, the sequences of the key primer and/or key probe needed for the unlocking vary. Therefore, for example, by setting up a plurality of dummy DNA sets in advance, it is possible to prepare a kit comprising combinations of DNAs necessary to cover all possible combinations of key primers and/or key probes corresponding to the sets of the dummy DNAs. Similarly as in the previous example, it is possible to specify a key primer necessary for unlocking by referring to the name of kit used for the unlocking.

Herein, cells collected from a living organism function not only as a sample containing genetic information, but also as a data source of genetic information. Therefore, for example, it is possible to produce copies of genetic information by culturing collected cells. Alternatively, prior to performing the decoding process, it is also possible to culture cells in a biological sample, proliferate them, and then extract the genetic information from the cultured cells. Therefore, in order to control genetic information, the prevention of culturing once the cells are collected, is also an important issue. For that purpose, a drug capable of killing the collected cells, or reversibly blocking the physiological activity thereof, may be added. The present invention also includes the locking by drugs to block the physiological activity of cells. Locking of genetic information by dummy DNAs, DNA polymerase inhibitors, and such, would most likely be inadequate for certain cell cultures. Therefore, the prevention of cell culture is effective in locking information.

For example, respiratory enzyme inhibitors and various antibiotics can be used to block the physiological activity of cells. Specifically, the addition of antibiotics and respiratory enzyme inhibitors that do not act on nucleic acids enables the irreversible blocking of the physiological activity of cells. As an antibiotic that does not act on nucleic acids, for example, Kanamycin, or derivatives thereof, can be used. Alternatively, as a respiratory enzyme inhibitor, cyanides are well known. Drugs that irreversibly block the physiological activity of cells will continue to inhibit cell culture, even after the cells are separated, and thus, a more secure locking of information can be expected. On the other hand, drugs that reversibly block the physiological activity of cells are useful in that they make unlocking of information possible by separating cells.

It is desirable to add these drugs to biological samples at sufficiently high concentrations so as to achieve a sure effect. Specifically, in the case of blocking the physiological activity of blood cells such as lymphocytes, and the like, using, for example, potassium cyanide as a drug, it is added to a final concentration of at least 1 μM or more, usually in the range of 5 to 500 μM. In practice, it is convenient to fill in advance, tools and vessels for collecting biological samples with these drugs at a concentration capable of achieving a sufficient action according to the expected amount of samples.

A biological sample is generally collected to obtain some sort of information. Therefore, it is desirable to prevent the analysis of genetic information based on the present invention, and, at the same time, not influence the necessary test as much as possible. For example, since the addition of dummy DNA is unlikely to influence most enzymatic reactions, it is a suitable technique for locking genetic information in the present invention. Nowadays, many biochemical tests of serum lipids, enzymes in blood, and such, are conducted based on enzymatic reactions, and such enzyme reactions are thought to be hardly influenced by nucleic acids in general.

The method for protecting personal information according to the present invention can be easily carried out by using a sample-collecting vessel that has been filled in advance with a component for obstructing the analysis. For example, blood-collecting vessels are commercially available. Such commercially available blood-collecting vessel are nowadays filled in advance with a variety of drugs such as serum separators, anticoagulants, glycolysis inhibitors, and the like according to the purpose for collecting blood. In addition to these drugs, a component that obstructs the analysis in the present invention may also be filled into the vessels. Using such vessels, the sample collection and personal information locking can be simultaneously achieved.

When a component for obstructing the analysis of a component that provides personal information to be protected is added to a biological sample based on the present invention, the fact that the component was added may be indicated depending on the need. Especially, when the unlocking of information is required, it is useful to indicate what sort of blocking has been done. However, needless to say, the indication should not be made in a form that makes the illegal unlocking by a third party easy. For example, when the dummy DNA is removed by the binding thereof to an affinity substance, the fact of locking may be indicated by a code that implies the affinity substance that has to be used for the unlocking.

In the present invention, there is no limitation in the types of means for indicating information on a sample-collecting vessel. Indication of information includes, for example, the printing of information directly on a sample vessel, pasting of a label on which information is printed, attachment of a magnetic medium in which information is recorded, etc. Furthermore, information may be indicated not only directly on the sample vessel itself, but also indirectly. Indirect indication of information includes, for example, indicating information on the rack that holds sample vessels, or on lids and covers of the vessels. Therefore, it is also possible to indicate information on the rack, and also specify each sample-collecting vessel by where it is arranged on the rack. Furthermore, information in the present invention includes not only lettered information, but also information that is distinguished by symbols and/or colors, or shapes, colors or materials of sample vessels, as well as the lids.

Furthermore, the present invention relates to a database correlating a biological sample-collecting vessel for protecting personal information obtained by analyzing a biological sample, wherein said vessel is filled in advance with a component that obstructs the analysis of another component that provides the personal information to be protected, with a means necessary for removing the influence of said obstructing component for each of the vessels. Database refers to a medium maintaining information in a machine-readable state, or a system that can be referred to as needed for information. Database of the present invention can be used by an organization that manufactured the biological sample-collecting vessels (containing a component that obstructs analysis based on this invention) to protect personal information, for the purpose of controlling a means necessary to perform accurate analysis without being influenced by the obstructing component for each of the vessels. Once a sample vessel is specified, information necessary for analysis can be obtained by referring to this database.

The Database is controlled by the organization that manufactured the biological sample-collecting vessels. The vessels are maintained so as not to disclose their contents unrestrictedly to the public. A third party who wants to analyze a biological sample in a sample-collecting vessel, can obtain necessary information by inquiring such an organization about information necessary for the analysis, or asking for permission to use the database as needed.

Database of the present invention can store together not only information necessary for conducting analysis without being influenced by an obstruction, but also information to assess the analytical result. Specifically, for example, in the case of disclosing information on primers for PCR, the length of the nucleotide sequence to be synthesized by said primers and number of nucleotide bands can be provided.

In the present invention, a means necessary for removing the influence of the above-described obstructing component for each vessel refers to the aforementioned means for unlocking. More specifically, the means can be exemplified by information specifying primers and DNA chips for PCR necessary for the accurate analysis or information required for removing the obstructing component. Information on primers, chips, and the like, which can be described in nucleotide sequences, can be directly disclosed. Alternatively, necessary information can be disclosed by specifying a particular nucleotide sequence out of a collection of predetermined nucleotide sequences.

Furthermore, not only nucleotide sequences, but also various conditions for performing more appropriate reactions can be also disclosed together. A more proper analysis can be done by unifying diverse conditions that are likely to influence the reaction into conditions that are hardly susceptible to the influence of the obstructing component.

Furthermore, the present invention provides a method for protecting personal information, wherein the method comprises the steps of:

(1) connecting (a) biological sample-collecting vessels for protecting personal information that can be obtained by analyzing a biological sample, wherein the vessels are filled in advance with a component that obstructs the analysis of another component that provides personal information to be protected, with (B) a means necessary for removing the influence of said obstructing component for each of the vessels, and (2) disclosing, according to a request from an individual who requires analysis, a means necessary for removing the influence of said obstructing component for a specific vessel.

Step (1) can be carried out, for example, by preparing the aforementioned database. Furthermore, in the present invention, a person in need of analysis refers to a subject from whom the biological sample has been collected, or an analysis organization that has been permitted by such a subject to do the analysis. Therefore, step (2) includes a step of certifying whether or not the person in need of analysis is actually the person to whom the disclosure of analytical conditions has been permitted. The certification step can be conducted, for example, using a certification code previously set up for each subject. More specifically, the certification can be performed using a password set up by the subject himself.

Furthermore, according to the present invention, a method for analyzing a biological sample is provided, wherein the method comprises:

a) reading an indication on a vessel for collecting a biological sample equipped with a means for indicating information capable of specifying said vessel for protecting personal information obtained by analyzing a biological sample, wherein said vessel has been filled in advance with a component that obstructs the analysis of another component that provides personal information to be protected, b) disclosing a means necessary for removing the influence of a obstructing component contained in said vessel by inquiring the database about information capable of specifying the vessel, c) implementing the means necessary for removing the obstruction based on information read in step b), and d) analyzing the sample.

In the present invention, information capable of specifying a vessel may be, for example, the manufactured lot number, or a number or symbol unique to each sample vessel. In the case where the specification relies on a lot number, it discloses to users an unlocking technique common to all the products within the same lot. Therefore, a more firm security can be expected by giving an indication unique to each vessel.

An indication specifying a vessel can be conferred by known techniques such as printing of letters, colors, symbols or bar-codes or using magnetic media, etc. These indications can be mechanically read.

Information necessary for analysis can be obtained by inquiring the above-described database about it based on the content of the indication means. Based on the information thus obtained, the analytical method of the present invention is carried out by implementing a means necessary for removing the obstruction and further analyzing the sample. In the present invention, the step of implementing a means necessary for removing the obstruction is, for example, the step of selecting primers required for analysis to make preparations for the analysis reaction. Once the preparation is completed, analysis can be carried out according to the usual analytical method. A series of such steps can be automated by an apparatus.

That is, the present invention relates to a sample-analyzing device provided with the following means:

a) a means for reading an indication on a biological sample-collecting vessel that (a) is equipped with a means for indicating information capable of specifying the vessel, and (b) is a biological sample-collecting vessel for protecting personal information obtained by analyzing a biological sample, wherein said vessel is filled in advance with a component that obstructs the analysis of another component that provides personal information to be protected, b) a means for disclosing a means necessary for removing the influence of an obstructing component contained in said vessel by inquiring the database about information capable of specifying the vessel;

c) a means for implementing the means disclosed by the means of b) that is necessary for removing the obstruction, and d) a means for analyzing the biological sample.

In the apparatus according to the present invention, the above-described database can be locally maintained by the apparatus, or the apparatus can inquire the database-controlling organization via a network. An organization that controls a database is, for example, an above-described organization that manufactured a sample vessel of the present invention. Alternatively, a duplicate of the database prepared by such an organization can be stored in a predetermined second organization. A database is so controlled that only a certified apparatus is permitted to refer to it. Thereby, security is maintained even when the database is mechanically referred.

The apparatus according to the present invention has a means for conducting a means necessary for removing the obstruction revealed by the means of b). The means c) includes, for example, a means for selecting appropriate primers necessary for PCR analysis and giving directions to the operator. Alternatively, it can be so designed that the apparatus initiates analysis by automatically selecting an appropriate primer(s) out of a plurality of primer sets previously set in the apparatus.

An embodiment of the protection of personal information and the use thereof based on the present invention is shown in FIG. 13, which is a schematic representation of the system constitution as described below. First, the "organization for protecting and controlling personal genome information" maintains information on sample-collecting vessels that have been filled in advance with a component that obstructs analysis, and, for each vessel, information on an analytical technique(s) that is not influenced by the obstructing component. Institutions entrusted with clinical tests, such as medical institutions and clinical test firms may know of the obstruction of genetic information analysis in the sample-collecting vessels. However, they have no information on how an unobstructed analysis can be conducted. Therefore, when the analysis of a sample is needed in a medical institution or an institution entrusted with clinical tests, they can request the "organization for protecting and controlling personal genome information" to disclose the information necessary for analysis with the consent of the individual who has provided the sample. In FIG. 13, this process is conducted through communication between the "genetic information analysis device with a security function" and database maintained by the "organization for protecting and controlling personal genome information". A network connects both systems. First, the "genetic information analysis device with a security function" specifies the sample collecting vessel whose analysis has been directed, and requests the database maintained by the "organization for protecting and controlling personal genome information" to disclose the information (unlocking code) necessary for analyzing the sample collected in the vessel. The database system maintained by the "organization for protecting and controlling personal genome information" discloses information necessary for the analysis after authorization by the "genetic information analysis device with a security function" according to the demand. The "genetic information analysis device with a security function" can proceed with the analysis of the sample based on the unlocking code thus disclosed under unobstructed conditions.

The patient who has provided a sample can permit the analysis thereof only to a specified "genetic information analysis device with a security function." Therefore, for example, even when the biological sample leaks out, accurate analysis cannot be conducted. Furthermore, for medical institutions and institutions entrusted with clinical tests who actually analyze the sample, no particular procedure to protect personal information is required since information necessary for obtaining the right result is automatically received by communications between the above devices. Therefore, the management of a large quantity of samples is not a big burden to these organizations.

In the present invention, information necessary for removing the influence of an obstructing means may be indicated directly on a sample-collecting vessel. That is, the present invention relates to a method for analyzing biological samples, in which the method comprises:

a) reading an indication on a biological sample-collecting vessel equipped with a means for indicating information necessary for removing the influence of an obstructing means, wherein said vessel for protecting the personal information obtained by analyzing said biological sample has been filled in advance with a component that obstructs the analysis of a component that provides the personal information to be protected, b) implementing a means necessary for removing the obstruction based on the information read in step a), and c) analyzing the sample.

For example, the indication on a vessel of a symbol that specifies primers necessary for analysis will allow users to know these primers. When a plurality of primer sets exist, the right primers cannot be selected unless the primer set corresponding to the sample vessel can be specified. Thus, a certain level of security can be expected. Furthermore, security can be further improved by encoding the indication. When the indication itself has been encoded, it is possible to even indicate the nucleotide sequence of primers necessary for analysis on the vessel.

The present invention also provides an analysis apparatus capable of carrying out the aforementioned analytical method. That is, this invention relates to a sample analysis apparatus provided with the following means:

a) a means for reading an indication on a biological sample-collecting vessel equipped with a means for indicating information necessary for removing the influence of an obstructing means, wherein said vessel for protecting personal information that can be obtained by analyzing a biological sample has been filled in advance with a component that obstructs the analysis of another component that provides personal information to be protected, b) a means for implementing a means necessary for removing the obstruction based on information read in step a), and c) a means for analyzing the test sample.

When the information necessary for removing the influence of the above-described obstructing means has been encoded, it is also possible to incorporate a means for decoding such codes into the apparatus of this invention. Alternatively, a means for inquiring via a network about information necessary for decoding such a code may be combined in the apparatus.

A means for analyzing a sample in such an apparatus refers to a system necessary for analyzing ordinary biological samples. Specifically, for example, the apparatus that aims to analyze nucleic acids may be provided with a mechanism for extracting a nucleic acid from blood cells, mixing the sample with necessary reagents to perform PCR, and analyzing results thus obtained. The apparatus according to the present invention may be provided with a mechanism for recording analytical results. Since the analytical method of this invention aims at protecting personal information, it is desirable to record analytical results only after encoding them.

BEST MODE FOR CARRYING OUT THE INVENTION

Figure 1:
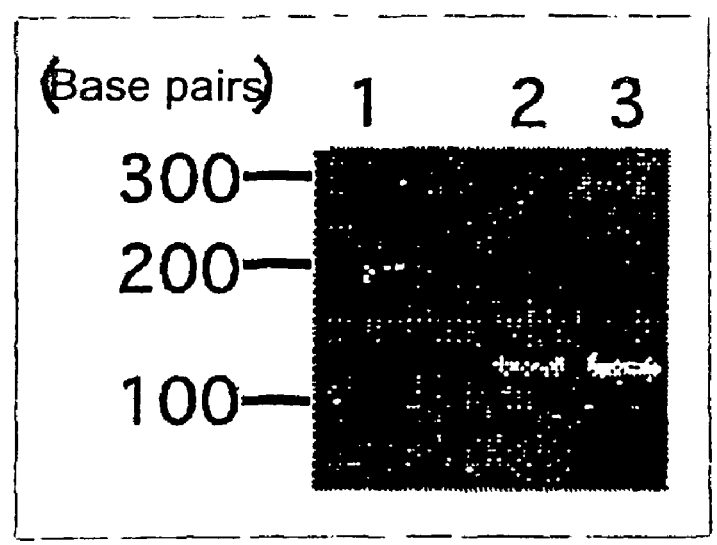
FIG. 1 is a photograph representing the amplification results for a ras gene fragment. Lane 1 shows the bands of DNA molecular weight markers, and lanes 2 and 3 represent amplification results without and with the addition of a dummy DNA, respectively.

Hereinbelow, the present invention will be specifically described with reference to Examples.

Example 1

Interfering With Oncogene Ras Detection Using Blood-collecting Tubes Containing Dummy DNAs Blood-collecting tubes into which any one of eight types of dummy DNAs had been added in advance and dried up were prepared. These DNAs comprise the region of 128 bp containing a portion of the c-Ki-ras gene, one of the proto-oncogenes, having the sequences set forth in the attached sequence listing. Each of the dummy DNAs is altered in any one of the nucleotides at the positions 68 to 70 of the DNA fragment (underlined section encoding the 61$^{st}$ codon of the Ras protein) from those of a normal healthy subject [wild type (WT)]. Nucleotides different from those of WT are described in capital letters in the sequence listing. Furthermore, in the sequences other than that of WT (SEQ ID NO: 1), the 61$^{st}$ amino acid encoded by that sequence are shown in parenthesis.

```
(WT)
5' ttcctaca ggaagcaagt agtaattgat ggagaaacct gtctcttgga   SEQ ID NO: 1 tattctcgac acagcaggtc  aagaggagta cagtgcaatg agggaccagt
                       ‾‾‾‾‾‾‾‾‾‾
```

-continued acatgaggac tggggagggc tttctttgtg (Lys)
5' ttcctaca ggaagcaagt agtaattgat ggagaaacct gtctcttgga    SEQ ID NO: 2 tattctcgac acagcaggtA aagaggagta cagtgcaatg agggaccagt acatgaggac tggggagggc tttctttgtg (Glu)
5' ttcctaca ggaagcaagt agtaattgat ggagaaacct gtctcttgga    SEQ ID NO: 3 tattctcgac acagcaggtG aagaggagta cagtgcaatg agggaccagt acatgaggac tggggagggc tttctttgtg (Arg)
5' ttcctaca ggaagcaagt agtaattgat ggagaaacct gtctcttgga    SEQ ID NO: 4 tattctcgac acagcaggtc Gagaggagta cagtgcaatg agggaccagt acatgaggac tggggagggc tttCtttgtg (Pro)
5' ttcctaca ggaagcaagt agtaattgat ggagaaacct gtctcttgga    SEQ ID NO: 5 tattctcgac acagcaggtc Cagaggagta cagtgcaatg agggaccagt acatgaggac tggggagggc tttctttgtg (Leu)
5' ttcctaca ggaagcaagt agtaattgat ggagaaacct gtctcttgga    SEQ ID NO: 6 tattctcgac acagcaggtc Tagaggagta cagtgcaatg agggaccagt acatgaggac tggggagggc tttctttgtg (His)
5' ttcctaca ggaagcaagt agtaattgat ggagaaacct gtctcttgga    SEQ ID NO: 7 tattctcgac acagcaggtc aTgaggagta cagtgcaatg agggaccagt acatgaggac tggggagggc tttctttgtg (His)
5' ttcctaca ggaagcaagt agtaattgat ggagaaacct gtctcttgga    SEQ ID NO: 8 tattctcgac acagcaggtc aCgaggagta cagtgcaatg agggaccagt acatgaggac tggggagggc tttctttgtg 0.3 μg each of the DNAs comprising the nucleotide sequences set forth in SEQ ID NOs: 1, 4, 5, and 6 in the sequence listing were added as dummy DNAs into blood-collecting tubes (containing heparin sodium) and dried. These dummy DNAs were modified at the 5'-end with biotin prior to use. Blood samples (3 ml each) collected from a healthy normal subject were placed in blood-collecting tubes containing dummy DNAs and an ordinary blood-collecting tube (containing no dummy DNA), and gently stirred using a rotator. After being left to stand at room temperature for 1 h, aliquots of the blood (0.1 ml each) were withdrawn from the blood-collecting tubes and placed in microtubes, and DNAs were extracted using a DNA extraction kit (Gen Torukun™, Takarashuzo). The polymerase chain reaction (PCR) was performed using as the template DNAs thus extracted in the following reaction system under the conditions described below. KOD-dash DNA polymerase (Toyobo) and a 10-fold-concentrated buffer attached to the kit were used in the PCR. PCR was performed by repeating 25 cycles of "94° C. 30 s, 52° C. 10 s, and 74° C. 30 s".

| PCR Reaction system | |
|---|---|
| Reaction solution composition | (μl) |
| Attached 10-fold concentrated buffer | 5 |
| 2 mM dNTP | 5 |
| Primer F (20 pmol/μl)* | 1 |
| Primer-D (20 pmol/μl)* | 1 |
| Template DNA (50 ng/μl) | 0.5 |
| KOD-dash DNA polymerase | 0.5 |
| Sterilized distilled water | 37 |
| Total | 50 |

*Nucleotide sequences of the primers are as follows.
Primer F: 5'-ttcctacaggaagcaagtag-3' (SEQ ID NO: 9)
Primer D: 5'-cacaaagaaagccctcccca-3' (SEQ ID NO: 10)

Figure 2:
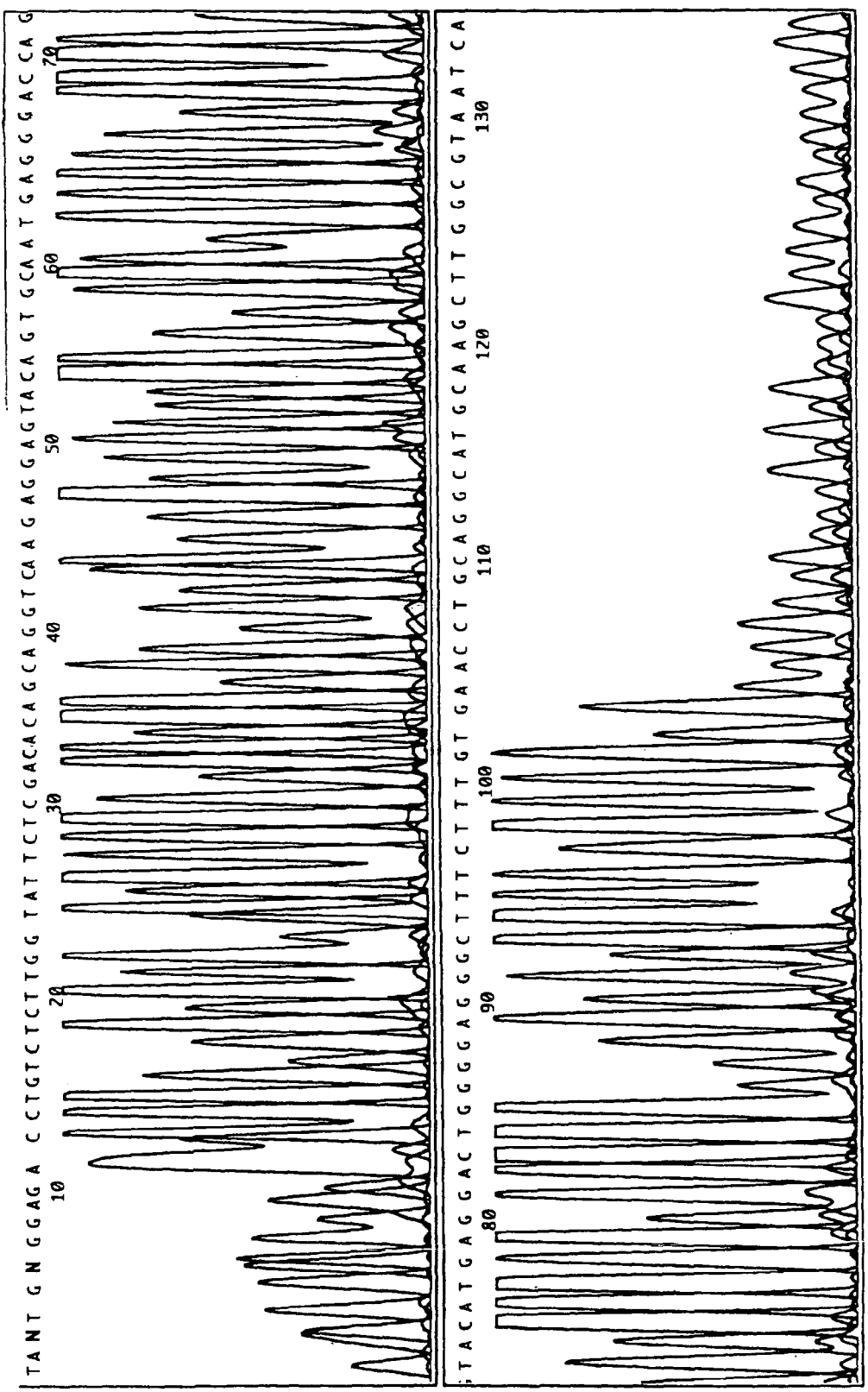
FIG. 2 represents analytical results of the nucleotide sequence (SEQ ID NO:20) of the fragment amplified using as the template, DNA derived from blood containing no dummy DNA. At each fluorescence intensity peak, the respective nucleotide analyzed from the peak is described. In the polymerase chain reaction (PCR) for the nucleotide sequence analysis, primer F was used.
Figure 3:
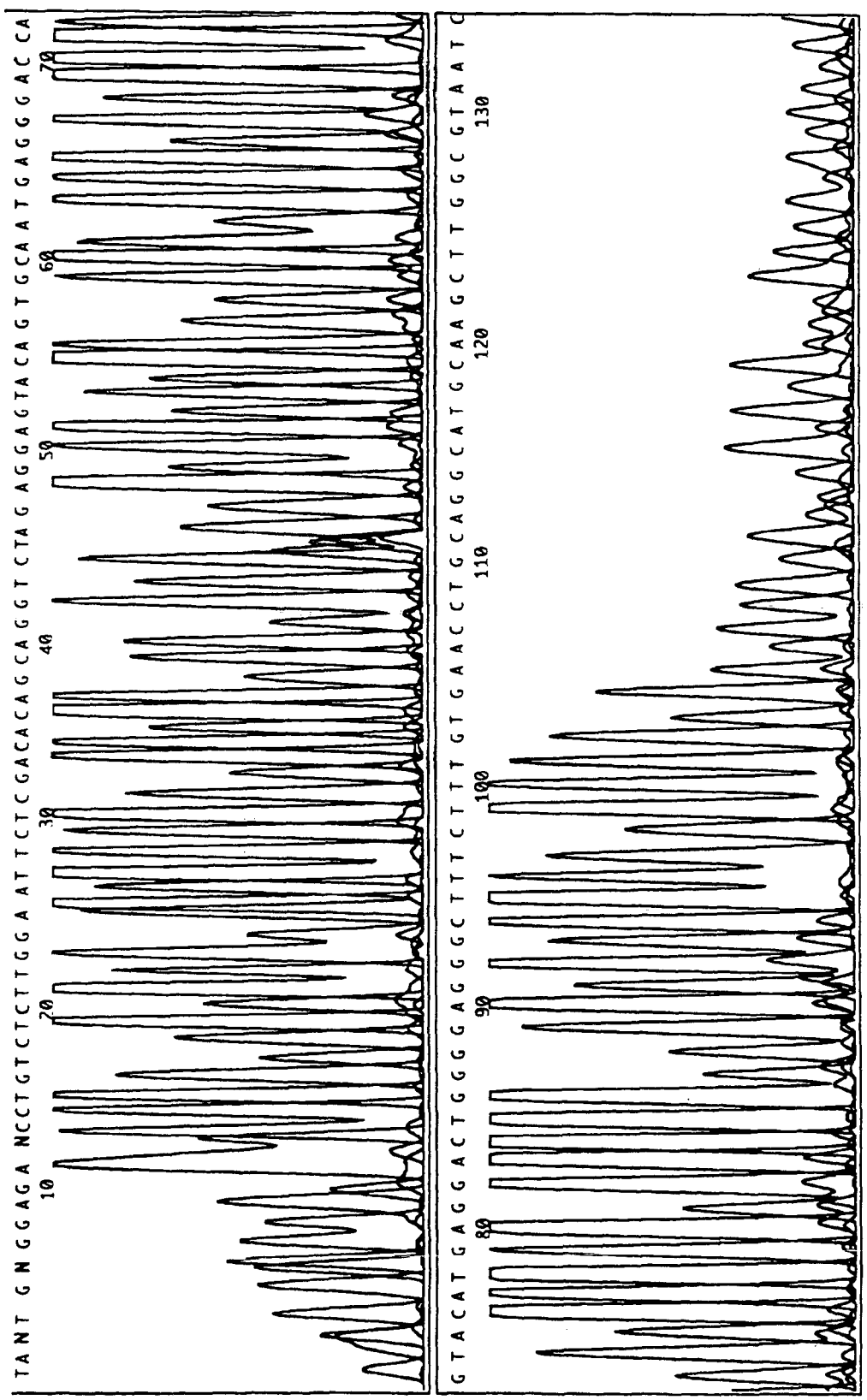
FIG. 3 represents analytical results of the nucleotide sequence (SEQ ID NO:21) of the fragment amplified using as the template, DNA derived from blood containing dummy DNA. At each fluorescence intensity peak, the respective nucleotide analyzed from the peak is described. In the polymerase chain reaction (PCR) for the nucleotide sequence analysis, primer F was used.

As a result of PCR, in every case in which a DNA extracted from a blood sample collected into a blood-collecting tube was used as a template, the amplification of a 128 bp DNA fragment was confirmed as shown in FIG. 1. Nucleotide sequences of DNA fragments thus amplified were analyzed using primer F and a BigDye terminator cycle sequence ready reaction kit (Perkin-Elmer) with an ABI 310 genetic analyzer (Perkin-Elmer). As shown in FIG. 2, the nucleotide sequence of the fragment amplified using as a template, DNA derived from blood collected in the ordinary blood-collecting tube was completely identical to that set forth in SEQ ID NO: 1 from 30 nucleotides downstream of the primer where the analytical results are apparent (FIG. 2). In contrast, the nucleotide sequence of the fragment amplified using as a template DNA derived from blood collected in blood-collecting tubes containing dummy DNAs, had intermingled signals at the site where the 4 types of dummies differed (the site encoding the 61$^{st}$ codon of the Ras protein), which made accurate reading of the nucleotide sequence impossible (FIG. 3). Namely, the sequence CAA in the healthy normal subject was erroneously read as CTA. Since the dummy DNAs have four different codons CAA, CTA, CCA, and CGA, it is clear that the four types of peaks were intermingled at the second nucleotide position of the codon as theoretically predicted. Thus, it is clear that the analysis of ras gene using a blood sample from a subject has been interfered with and locked by using a blood sample-collecting tube containing dummy DNAs.

Example 2

Unlocking of Genome Information

Next, it was confirmed that the unlocking can be done and the original information can be read by removing the interfering factor (dummy DNA) from the information on the nucleotide sequence that has been locked by the interference. Since dummy DNAs are modified with biotin, they can be removed using magnetic beads binding streptavidin.

Figure 4:
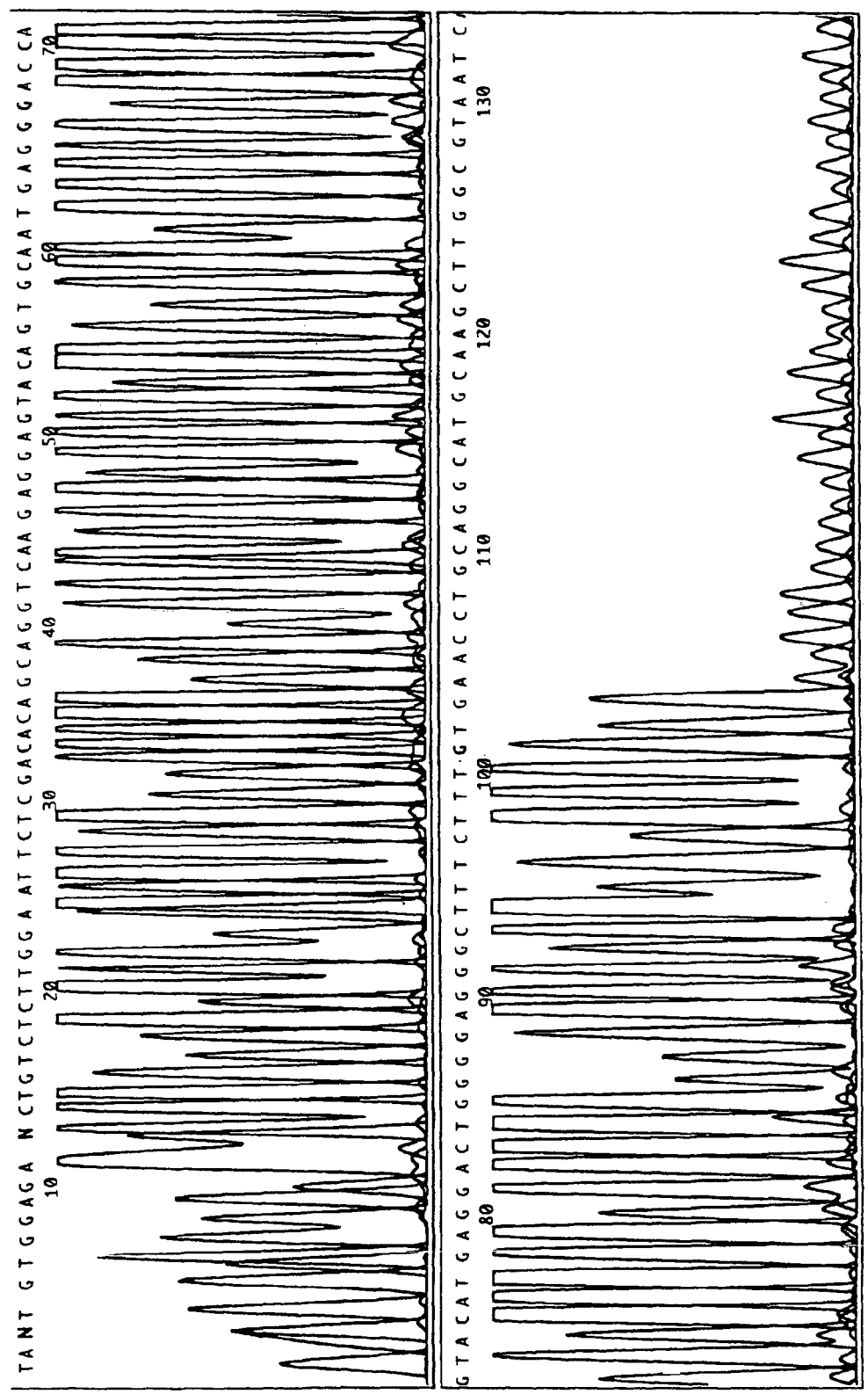
FIG. 4 represents analytical results of the nucleotide sequence (SEQ ID NO:22) of the fragment amplified using as the template, DNA derived from blood from which the added dummy DNA has been removed using streptavidin-bound magnetic beads. At each fluorescence intensity peak, the respective nucleotide analyzed from the peak is described. In the polymerase chain reaction (PCR) for nucleotide sequence analysis, primer F was used.

Magnetic beads bound to streptavidin (Dynabeads M-280 Streptavidin (DYNAL)) (0.15 ml) were transferred into a microtube, and separated from the supernatant on a magnet stand. The supernatant was discarded, and, after washing beads with B & W buffer (10 mM Tris-HCl, pH 7.5, 1 mM EDTA, 2 M NaCl), the DNA (50 µl, ca 0.3 µg) derived from the blood in the blood-collecting tube containing B & W buffer (50 µl) and dummy DNA was mixed with the magnetic beads. After the resulting mixture was left to stand at room temperature for 15 min, the supernatant was separated from beads on a magnetic stand and recovered. PCR was performed similarly as in Example 1 using as a template DNA contained in the supernatant, and the nucleotide sequence of the DNA fragment thus amplified was analyzed with an ABI 310 genetic analyzer (Perkin-Elmer) using primer F and a Big Dye terminator cycle sequence ready reaction kit (Perkin-Elmer). The results are shown in FIG. 4.

Results show that streptavidin bound to magnetic beads binds to biotinized dummy DNA to almost completely trap the dummy DNA onto the bead surface so that intermingled signals observed in the locked state are completely absent. That is, the supernatant contained only DNA derived from the subject's blood so that the signal of CAA (the part encoding the 61$^{st}$ codon of Ras protein), the sequence in the ras gene of the healthy normal subject, could be confirmed. These results proved that it was actually possible to unlock locked genomic information by performing the specific method for removing the chemically modified dummy DNA.

Example 3

Locking of Information Using Eight Different Types of Dummy DNAs and the Influence of the Amount of Dummy DNA Next, types of dummy DNA added to the blood-collecting tube were increased, and the locking was conducted using all the eight types. Using the same method as in Example 1, blood was collected into a blood-collecting tube containing eight types of dummy DNAs (0.3 µg each) to extract DNA. In this case, however, the amount ratios of dummy DNAs to be added into the blood-collecting tube were varied as shown in Table 1, and changes in signals were observed.

Figure 5:
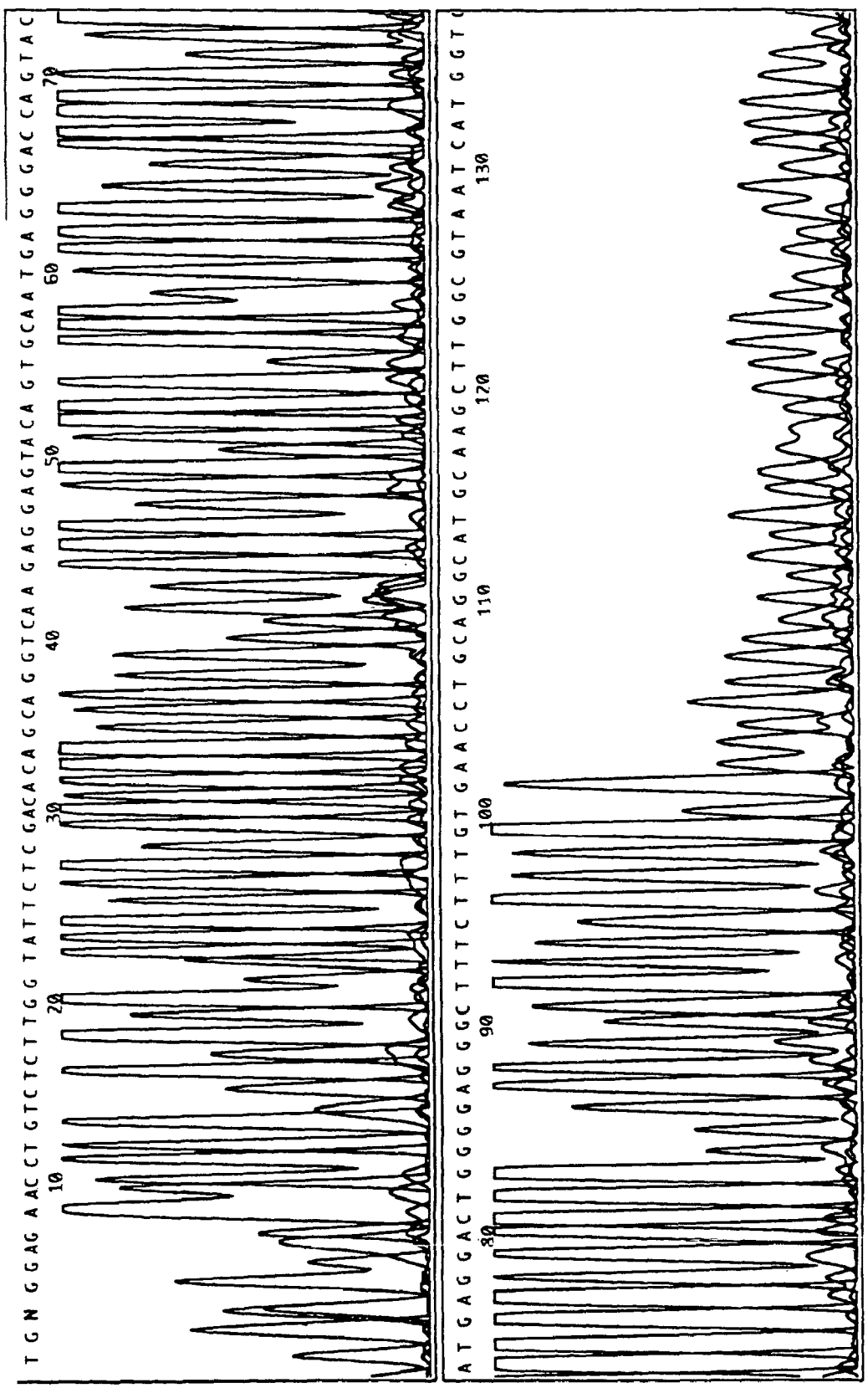
FIG. 5 represents analytical results of the nucleotide sequence (SEQ ID NO:23) of the fragment amplified using as the template, DNA derived from blood to which a dummy DNA (equal amount) has been added. At each fluorescence intensity peak, the respective nucleotide analyzed from the peak is described. In the polymerase chain reaction (PCR) for nucleotide sequence analysis, primer F was used.

The results are as shown in FIG. 5. In the case where DNAs set forth in SEQ ID NOs: 2 and 4 were added 3.5-folds more than other DNA sequences (FIGS. 6 and 7 respectively) or in an equal amount (FIG. 5), signals were all judged as CAA, the signal of the wild type. In spite of the presence of DNAs set forth in SEQ ID NO: 2 (nucleotides 68 to 70: AAA) and SEQ ID NO: 4 (nucleotides 68 to 70: CGA) in an amount that is 3.5-folds more than other DNA sequences, all of them were detected as the wild type sequence. That is, even in the case where a particular DNA sequence other than the wild type DNA is intermingled in a 3.5-fold excess, the detected sequences were all that of the wild type (CAA), similarly as in the case of mixing an equal amount of the respective dummy DNA.

This is thought to be due to the fact that, with the increase in the types of dummy DNA, among the respective nucleotides at the 68$^{th}$, 69$^{th}$, and 70$^{th}$ positions, the signal of the nucleotide with the strongest presence was emitted more strongly than others (cf. Table 2). Furthermore, the ras gene derived from blood in this Example is of the wild type (SEQ ID NO: 1), while the respective dummy DNAs are present in a large excess over the ras gene derived from the blood sample, and therefore, the sequence (CAA) obtained by the nucleotide sequence analysis is likely to be derived from dummy DNAs, and not from the blood. From the above-described facts, it is clear that if dummy DNAs having a wild-type sequence were present in excessive amounts, they would function to cover up mutant sequences. That is, even if there was a mutation in DNA derived from blood, the predominance of an excessive amount of dummy DNAs having a wild-type sequence, would lead to a more secure locking of the genomic information to an extent that makes it difficult to confirm even whether the genomic information is locked or not.

TABLE 1

Figure 6:
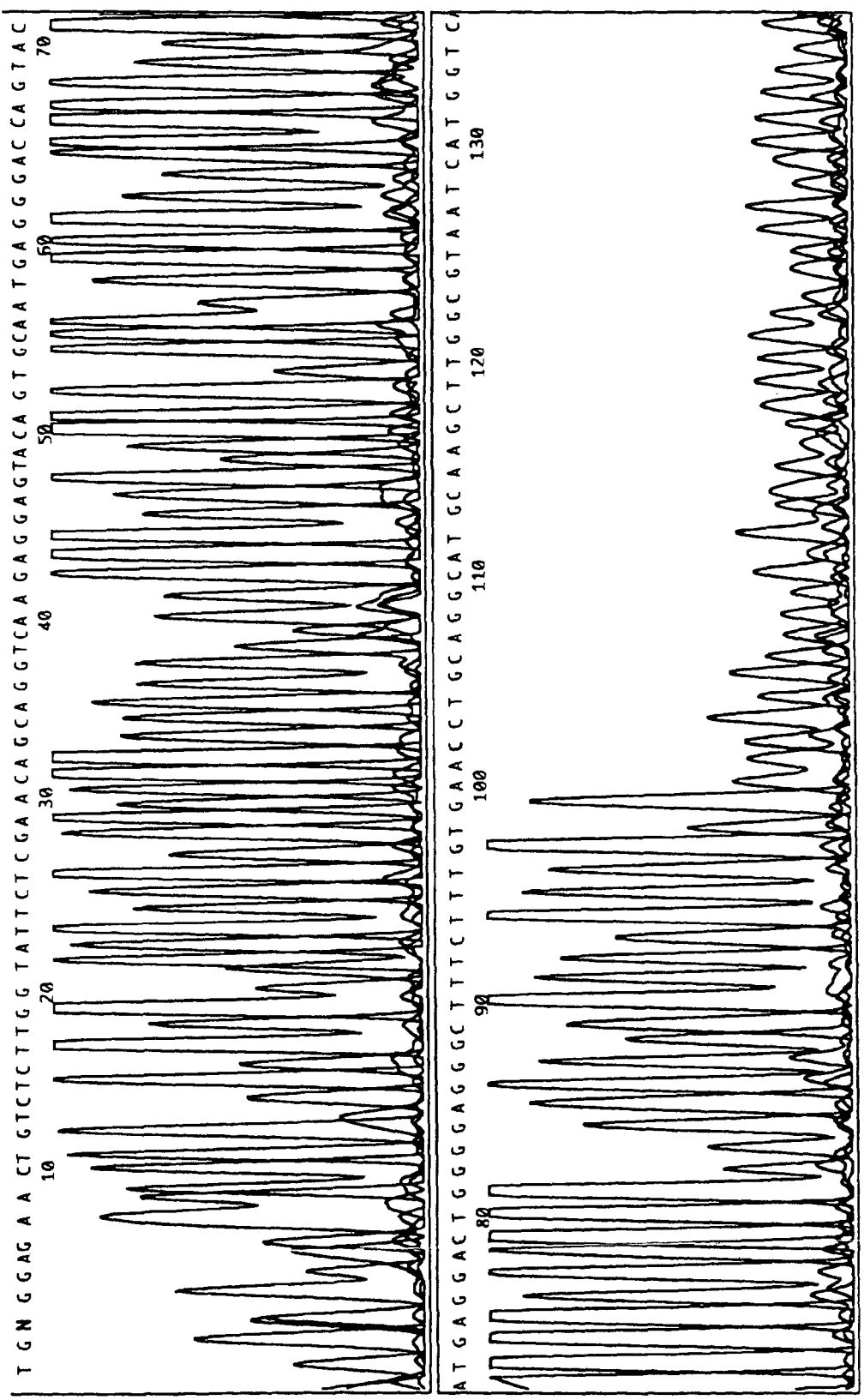
FIG. 6 represents analytical results of the nucleotide sequence (SEQ ID NO:24) of the fragment amplified using as the template, DNA derived from blood to which a dummy DNA (3.5-fold excess) has been added. At each fluorescence intensity peak, the respective nucleotide analyzed from the peak is described. In the polymerase chain reaction (PCR) for nucleotide sequence analysis, primer F was used.
Figure 7:
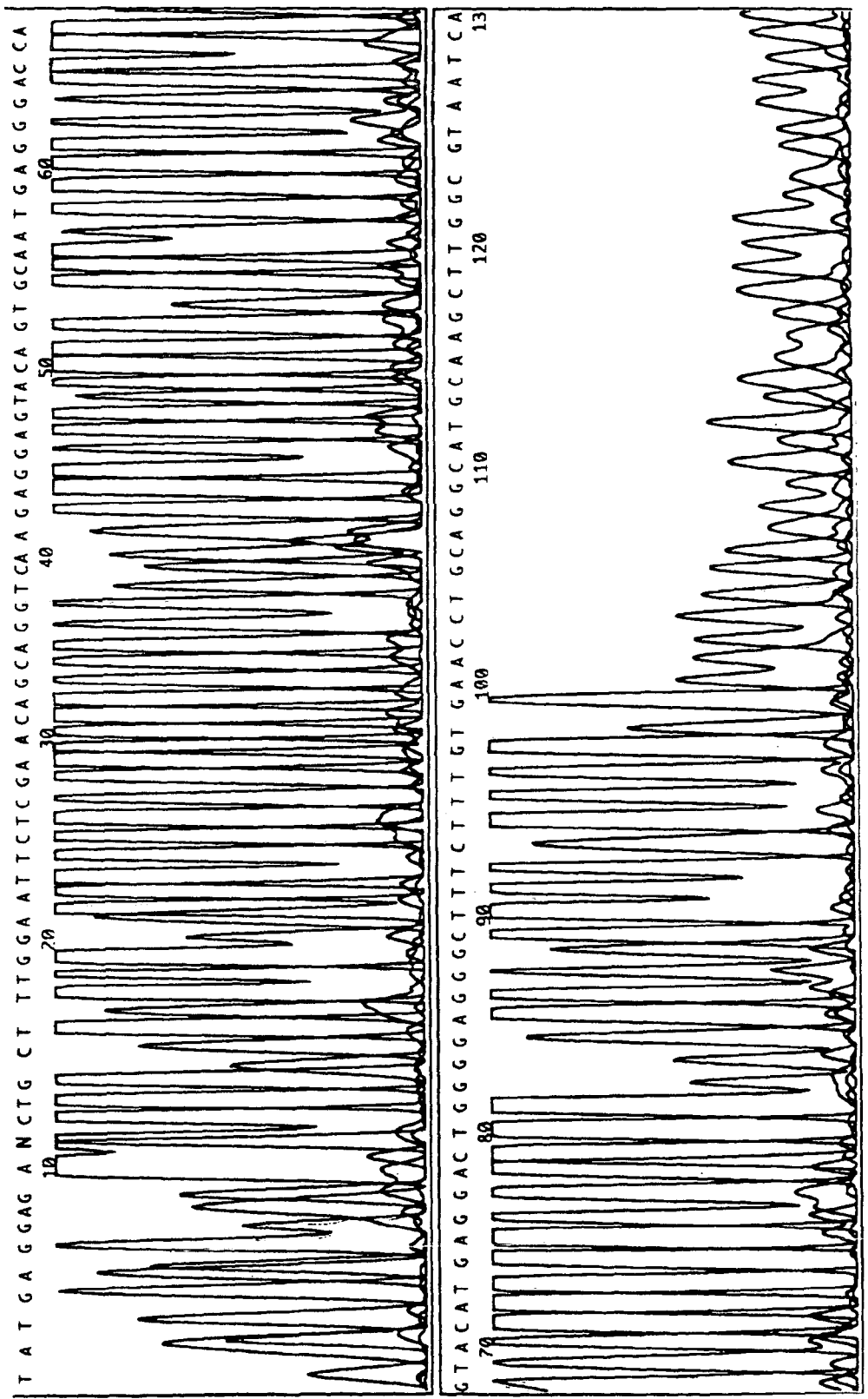
FIG. 7 represents analytical results of the nucleotide sequence (SEQ ID NO:25) of the fragment amplified using as the template, DNA derived from blood to which a dummy DNA (3.5-fold excess) has been added. At each fluorescence intensity peak, the respective nucleotide analyzed from the peak is described. In the polymerase chain reaction for nucleotide sequence analysis, primer F was used.

| | SEQ ID NOs | | | | | | | |
|---|---|---|---|---|---|---|---|---|
| FIGS. | 1 | 2 | 3 | 4 | 5 | 6 | 7 | 8 |
| FIG. 5 | 1 | 1 | 1 | 1 | 1 | 1 | 1 | 1 |
| FIG. 6 | 1 | 3.5 | 1 | 1 | 1 | 1 | 1 | 1 |
| FIG. 7 | 1 | 1 | 1 | 3.5 | 1 | 1 | 1 | 1 |

TABLE 2

| | Nucleotide composition (%) | | | |
|---|---|---|---|---|
| Nucleotide | G | C | A | T |
| 68$^{th}$ nucleotide | 12.5 | 75.0 | 12.5 | 0 |
| 69$^{th}$ nucleotide | 12.5 | 12.5 | 62.5 | 12.5 |
| 70$^{th}$ nucleotide | 0 | 12.5 | 75.0 | 12.5 |

Example 4

Locking and Unlocking of Information Using Dummy DNA Chemically Modified With a Substance Other Than Biotin (in the Case of Using Digoxigenin)

Figure 8:
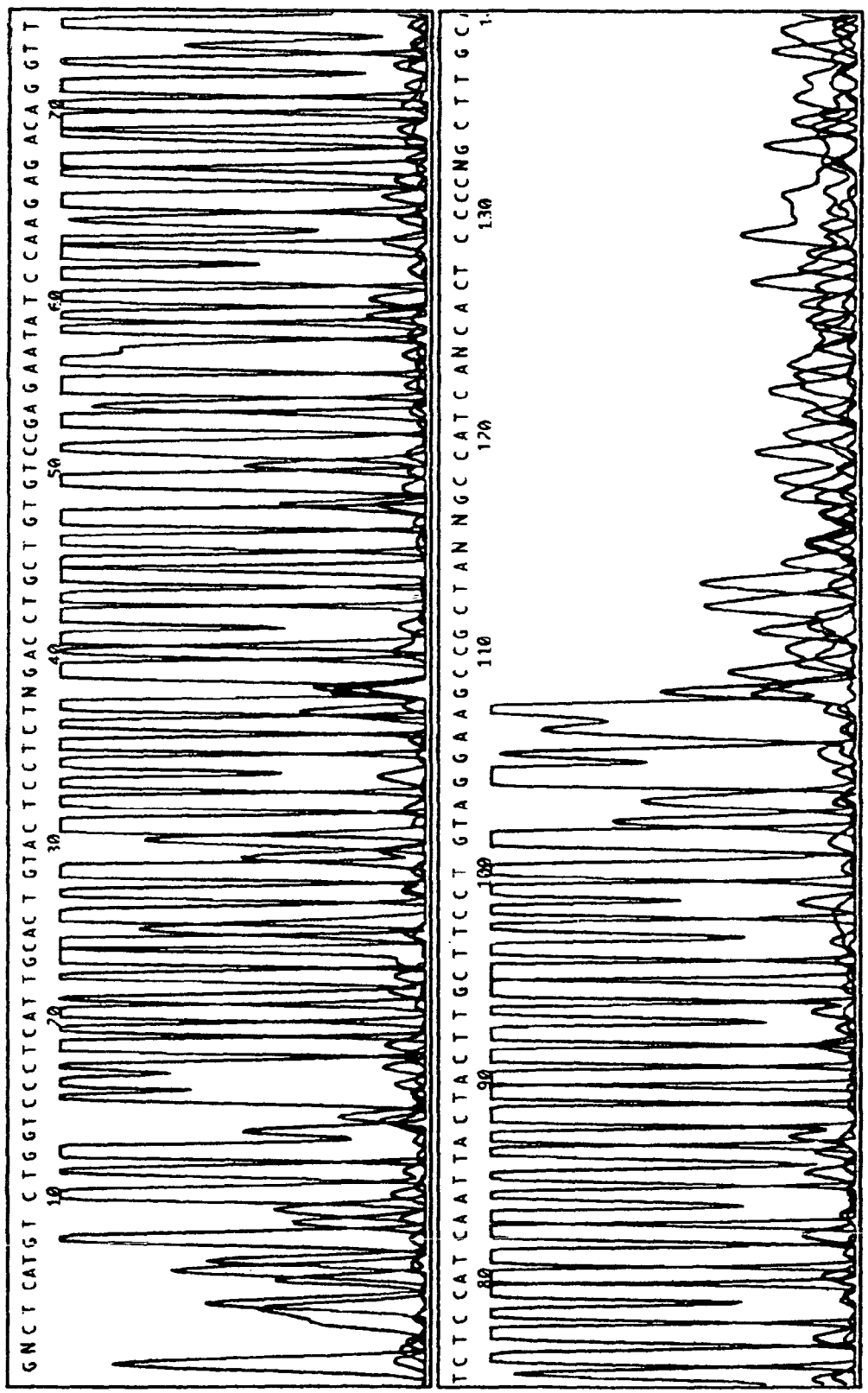
FIG. 8 represents analytical results of the nucleotide sequence (SEQ ID NO:26) of the fragment amplified using as the template, DNA derived from blood to which a dummy DNA has been added. At each fluorescence intensity peak, the respective nucleotide analyzed from the peak is described. In the polymerase chain reaction (PCR) for nucleotide sequence analysis, primer D was used.

The information of c-Ki-ras gene was locked similarly as in Example 1 using a dummy DNA modified at the 5'-end thereof with digoxigenin. Into a blood-collecting tube, the wild type DNA (0.3 µg) (SEQ ID NO: 1) and a mixture of equal amounts of dummy DNAs (SEQ ID NOs: 4, 5, 6, and 7) were added in an amount that was 3-folds the amount of wild type DNA (1 µg) to lock the wild type genetic information. Using the resulting mixture as a template, PCR was carried out using primers F and D by the same method as in Example 1. Using the DNA fragment thus amplified as a template, the nucleotide sequence thereof was analyzed using primer D by the same method as in Example 1, and, as a result, the signal interference as shown in FIG. 8 was confirmed, and the 69$^{th}$ nucleotide could not be determined.

Figure 9:
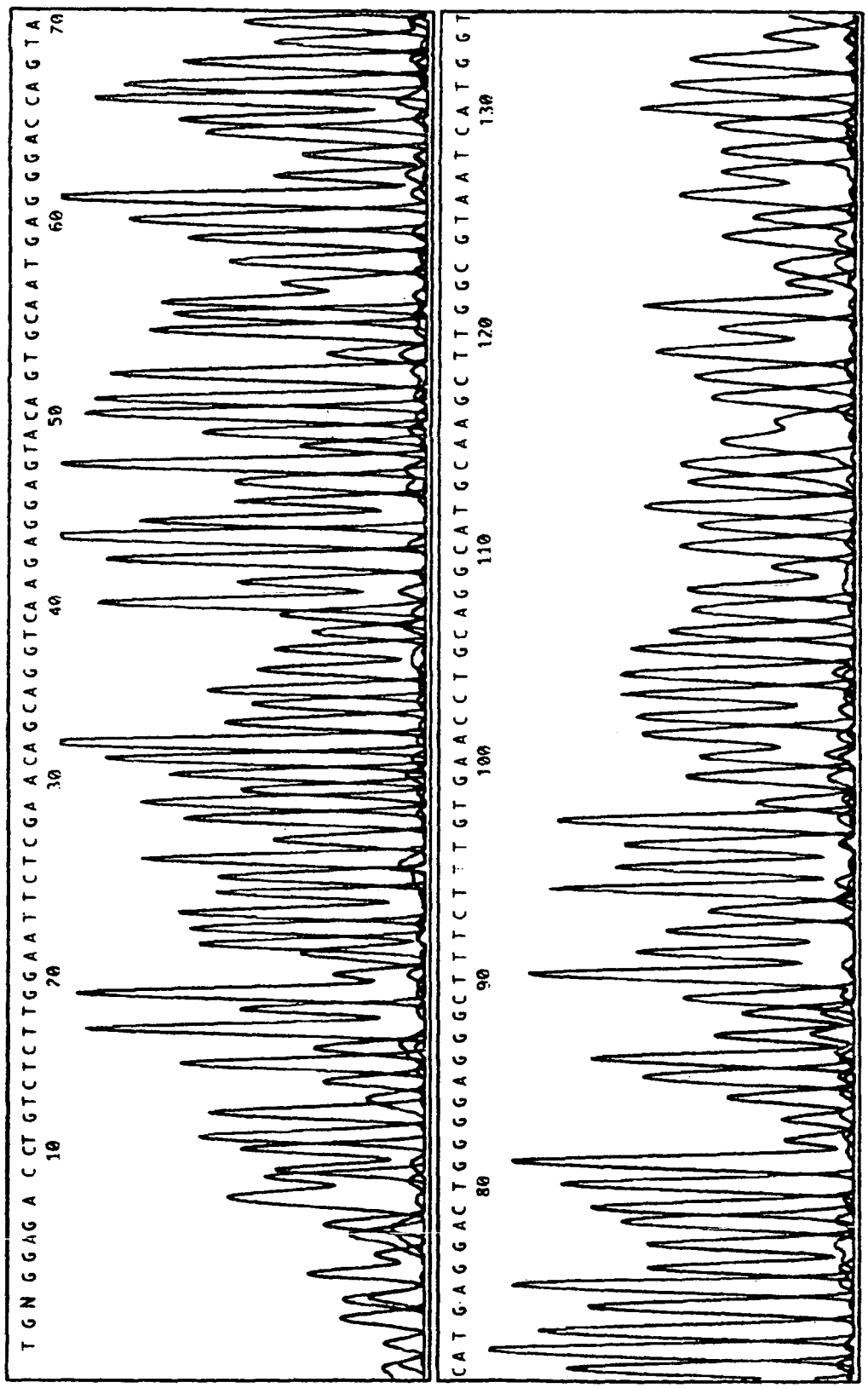
FIG. 9 represents the analytical results of the nucleotide sequence (SEQ ID NO:27) of the fragment amplified using as the template, DNA derived from blood, from which the added dummy DNA has been removed using protein G-Sepharose. At each fluorescence intensity peak, the respective nucleotide analyzed from the peak is described. In the polymerase chain reaction (PCR) for nucleotide sequence analysis, primer F was used.
Figure 10:
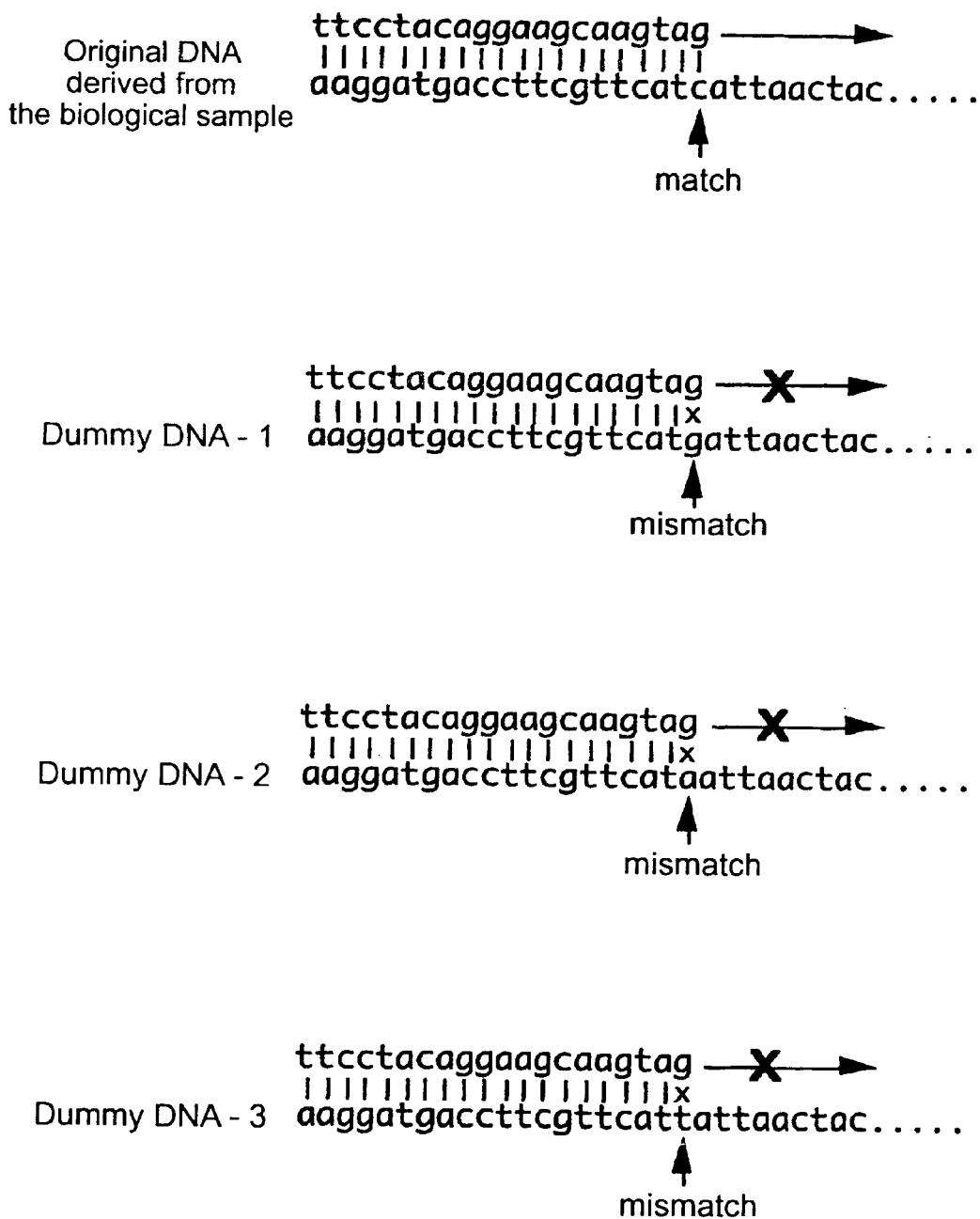
FIG. 10 is a schematic representation of the mechanism of the selective amplification of DNA derived from a living organism using a key primer (SEQ ID NOS:9 and 28-31).

Then, the anti-digoxigenin antibody (Boehringer-Mannheim) (20 µl) was added to the above-described mixture, followed by protein G Sepharose (Amersham-Pharmacia) (ca 30 µg). The resulting mixture was incubated at 37° C. for 10 min and then centrifuged at 3,000×g for 1 min to precipitate and remove the dummy DNA as a complex with the antibody and protein G Sepharose. Then, using the supernatant thereof (1 µl) as a template, PCR was performed by the same method as in Example 1. Using the sample (3 µl) after PCR as a template, and primer F, the nucleotide sequence of the sample was analyzed by the same method as in Example 1. As a result, as shown in FIG. 9, the signal interference of the 69$^{th}$ nucleotide disappeared, and the right nucleotide A (as is in the wild type DNA) became clearly readable. That is, it was proved that the chemically modified dummy DNA was specifically recognized by the antibody, an affinity substance for the modified site, and the dummy DNA was almost completely removed as a precipitate by protein G Sepharose, which has affinity towards the antibody.

Example 5

Next, the unlocking of wild type DNA (SEQ ID NO: 1) that had been locked using dummy DNAs having single nucleotide substitutions in the wild type DNA sequence was conducted. As dummy DNA, an equimolar mixture of the following sequences was used. Mutant portions (portions different from the wild type) of the respective dummy DNAs were all described in capital letters, and the substituted portions to influence the specificity of the key primers in this Example were underlined. SEQ ID NO: 11 (SEQ ID NO: 4 having two single nucleotide substituted portions)

```
ttcctacagg aagcaagtaA taattgatgg agaaacctgt
ctcttggata ttctcgacac agcaggtcGa gaggagtaca
gtgcaatgag ggaccagtac atgaggacAg gggagggctt
tctttgtg
```

SEQ ID NO: 12 (SEQ ID NO: 4 having two single nucleotide substituted portions)

```
ttcctacagg aagcaagtaC taattgatgg agaaacctgt
ctcttggata ttctcgacac agcaggtcGa gaggagtaca
gtgcaatgag ggaccagtac atgaggacCg gggagggctt
tctttgtg
```

SEQ ID NO: 13 (SEQ ID NO: 4 having two single nucleotide substituted portions)

```
ttcctacagg aagcaagtaC taattgatgg agaaacctgt
ctcttggata ttctcgacac agcaggtcGa gaggagtaca
gtgcaatgag ggaccagtac atgaggacAg gggagggctt
tctttgtg
```

SEQ ID NO: 14 (SEQ ID NO: 6 having two single nucleotide substituted portions)

```
ttcctacagg aagcaagtaA taattgatgg agaaacctgt
ctcttggata ttctcgacac agcaggtcTa gaggagtaca
gtgcaatgag ggaccagtac atgaggacAg gggagggctt
tctttgtg
```

SEQ ID NO: 15 (SEQ ID NO: 6 having two single nucleotide substituted portions)

```
ttcctacagg aagcaagtaC taattgatgg agaaacctgt
ctcttggata ttctcgacac agcaggtcTa gaggagtaca
gtgcaatgag ggaccagtac atgaggacCg gggagggctt
tctttgtg
```

SEQ ID NO: 16 (SEQ ID NO: 6 having two single nucleotide substituted portions)

```
ttcctacagg aagcaagtaC taattgatgg agaaacctgt
ctcttggata ttctcgacac agcaggtcTa gaggagtaca
gtgcaatgag ggaccagtac atgaggacAg gggagggctt
tctttgtg
```

SEQ ID NO: 17 (SEQ ID NO: 5 having two single nucleotide substituted portions)

```
ttcctacagg aagcaagtaA taattgatgg agaaacctgt
ctcttggata ttctcgacac agcaggtcCa gaggagtaca
gtgcaatgag ggaccagtac atgaggacAg gggagggctt
tctttgtg
```

SEQ ID NO: 18 (SEQ ID NO: 5 having two single nucleotide substituted portions)

```
ttcctacagg aagcaagtaC taattgatgg agaaacctgt
ctcttggata ttctcgacac aqcaggtcCa gaggagtaca
gtgcaatgag ggaccagtac atgaggacCg gggagggctt
tctttgtg
```

SEQ ID NO: 19 (SEQ ID NO: 5 having two single nucleotide substituted portions)

```
ttcctacagg aagcaagtaC taattgatgg agaaacctgt ctcttggata ttCtcgacac agcaggtcCa gaggagtaca gtgcaatgag ggaccagtac atgaggacAg gggagggctt tctttgtg
```

Using the wild type DNA (SEQ ID NO: 1) as a DNA derived from a biological sample, the locking was done by mixing with an equimolar mixture of dummy DNAs set forth in SEQ ID NOs: 11 through 19 at a molar ratio of 1:3 (Example 4-1) or 1:9 (Example 4-2). In order to examine whether the unlocking of a DNA sample locked in this state can be securely carried out or not, amplification by PCR was conducted with a 50-fold diluted DNA sample (1 μl, 7.1 fmol) that had been locked as a template using the key primers comprising the nucleotide sequences set forth in SEQ ID NOs: 9 and 10. Furthermore, a sample containing only the wild type DNA set forth in SEQ ID NO: 1 as a template in the same amount as in Example 4-1 and 4-2 (Comparative Example 4-0), and another sample containing only the dummy DNAs set forth in SEQ ID NOs: 11 through 19 in the same amount as in Example 4-1 and 4-2 (Comparative Example 4-3) were prepared, and PCR was performed similarly as in Examples.

The key primers (20 pmol) and 0.2 mM dNTP were added to the PCR system (50 μl), and as a thermostable DNA polymerase, Taq DNA polymerase (Sigma, 1 unit) was used. PCR was performed, after the treatment at 94° C. for 1 min, by 19 reaction cycles of "94° C. 30 s, 55° C. 30 s, and 72° C. 1 min". At the $10^{th}$, $13^{th}$, $16^{th}$, and $19^{th}$ cycle, samples (10 μl each) were withdrawn, and aliquots (3 μl each) were subjected to 5% polyacrylamide gel electrophoresis for analysis (FIG. 11).

Figure 11:
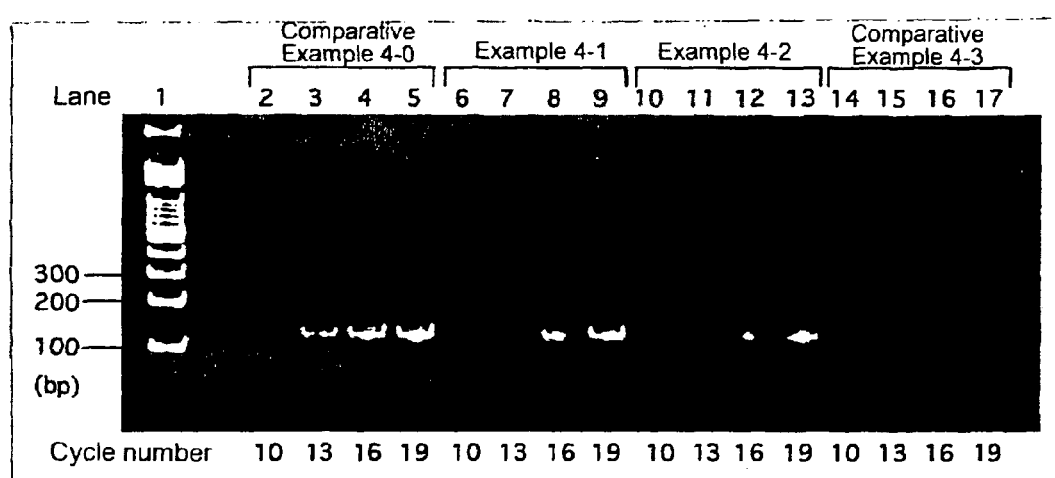
FIG. 11 is an electrophoretogram representing the result of the selective amplification of wild type DNA using a key primer.

As a result of electrophoresis, in the case of the Comparative Example 4-0 in which only the wild type DNA served as a template, the amplification of the target DNA fragment could already be confirmed at the $10^{th}$ cycle of PCR (FIG. 11, lane 2), the concentration of the amplified DNA having increased with the increase in the number of cycles (FIG. 11, lanes 3 to 5). In contrast to this, in the case where a mixture of dummy DNAs combined with the wild type DNA in a ratio of 3:1 (the concentration of the wild type DNA was ⅓ of that in Comparative Example 4-0) was used as a template, a slight amplification could be barely confirmed at the $10^{th}$ cycle (FIG. 11, lane 6) with the amplifications at relatively low concentrations compared to that of Comparative Example 4-0 even at the $13^{th}$ and $16^{th}$ cycles (FIG. 11, lanes 7 to 9). Furthermore, in the case where the dummy DNAs were mixed with the wild type DNA in a ratio of 9:1 (the concentration of the wild type DNA was ⅑ of that in Comparative Example 4-0) amplifications of relatively low concentrations compared to that of Comparative Example 4-0 were observed throughout all cycles with the amplification levels being lower than in Example 4-1 (FIG. 11, lanes 10 to 13). Moreover, in the case where only the dummy DNAs were mixed to serve as a template (Comparative Example 4-3), the amplification of target DNA fragment was not observed (FIG. 11, lanes 14 to 17) at all.

From the aforementioned results, a DNA amplified using the key primers is thought to be comprised solely of the wild type DNA set forth in SEQ ID NO: 1. The basis for this conclusion are the facts that the concentration of fragments amplified by PCR were dependent on the concentration of the wild type DNA contained in the original template, and that there was no amplification in PCR performed solely using the dummy DNAs as template.

Figure 12:
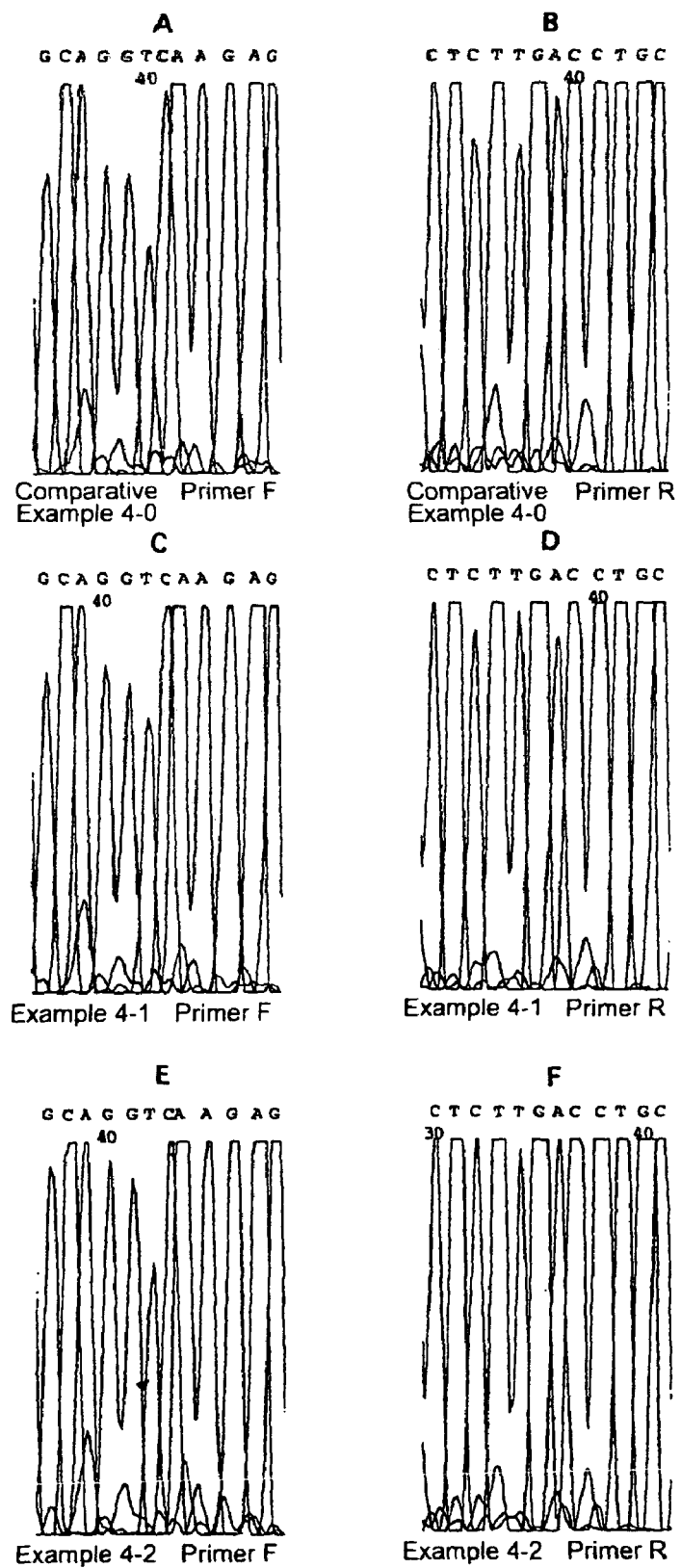
FIG. 12 represents the analytical result of the nucleotide sequences (SEQ ID NOS:32 and 33) of amplified DNAs shown in FIG. 11. At each fluorescence intensity peak, the respective nucleotide analyzed from the peak is described.
Figure 13:
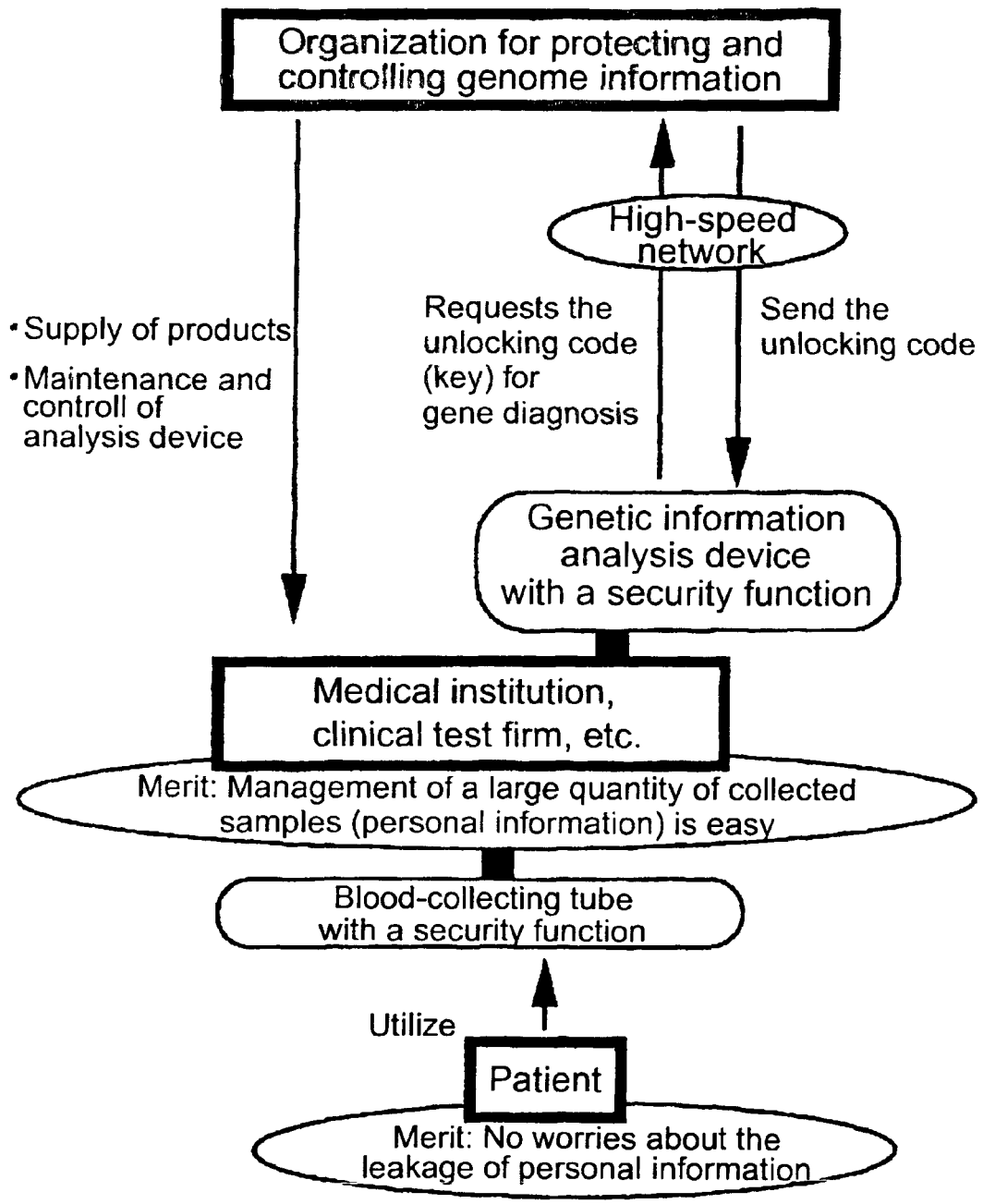
FIG. 13 is a diagram describing the mechanism of protecting personal information and utilizing the protected information based on the present invention.

Furthermore, DNA fragments amplified by 19 cycles of PCR in the respective Examples and the Comparative Example 4-0 were sequenced to examine whether they actually have the wild type sequence or not. As shown in panels A and B in FIG. 12, it is natural that fragments amplified with a template solely comprising the wild type DNA (Comparative Example 4-0) show the wild type sequence. However, it was found that, as shown in panels B and C as well as panels D and E in FIG. 12, when DNAs were amplified using templates comprising the wild type DNA mixed with a 3-fold and 9-fold excessive amounts of the dummy DNAs (Examples 4-1 and 4-2, respectively), DNA having the wild type nucleotide sequence was amplified similarly as in the Comparative Example 4-0. Thus, the results of sequencing proved a possibility that only the wild type DNA is selectively amplified using the key primers and that the information is actually unlocked using the key primers.

INDUSTRIAL APPLICABILITY

The present invention makes it possible to actively prevent the analysis of personal information that the subject does not intend to perform. Despite the fact that biological samples represented by blood are the source of important personal information, at present, the security thereof has been entrusted to only protection by operation rules and morals. That is, it can be said that, although personal information is an individual's own information, the management of the information has been entirely entrusted to strangers. The present invention makes it possible to control the security of personal information actively by oneself. A method for technically as well as securely protecting information that can be obtained from biological samples has been achieved for the first time by the present invention.

With the arrival of the postgenomic era, the speed of genetic information analysis is expected to dramatically increase. With the progress of genetic information analysis, the importance of genetic information will become increasingly enhanced. According to the present invention, the analysis of personal information that the person does not wish to analyze can be securely prevented so as to enable the maintenance of the security of information.

The invention claimed is:

1. A method for protecting personal information obtained by analyzing a biological sample from an individual, comprising adding to the biological sample a component that interferes with sequencing of a target nucleic acid from the individual in the biological sample, wherein the component comprises four polynucleotides, each of the four polynucleotides comprising a portion of the target nucleic acid that comprises a predetermined position, and wherein each of the four polynucleotides has a different nucleotide at the predetermined position, thereby preventing the nucleotide at the predetermined position of the target nucleic acid from being determined by sequencing.

2. The method of claim 1, wherein the component is removable from the sample.

3. The method of claim 2, wherein the four polynucleotides are biotinylated.

4. The method of claim 1, wherein the adding is achieved by introducing the component into a container prior to the biological sample being placed in the container.

5. The method of claim 1, wherein each of the four polynucleotides is greater in quantity compared to the target nucleic acid in the sample.

6. The method of claim 5, wherein each of the four polynucleotides is at least three times in quantity compared to the target nucleic acid in the sample.

7. The method of claim 1, wherein each of the four polynucleotides is present at about the same quantity.

8. The method of claim 1, wherein the target nucleic acid comprises genomic DNA of the individual.

9. The method of claim 1, wherein the biological sample is blood, sperm, mucus, saliva, bile, gastric juice, sweat, urine, or feces, or a tissue derived from an organ, skin, mucous membrane, hair, tooth, or nail.

10. The method of claim 1, wherein the sequencing of the target nucleic acid comprises an amplification technique selected from the group consisting of polymerase chain reaction (PCR), rolling circle amplification (RCA), nucleic acid sequence based amplification (NASBA), and strand displacement amplification (SDA).

11. The method of claim 10, wherein the sequencing of the target nucleic acid comprises PCR.

* * * * *